(12) United States Patent
Griffith

(10) Patent No.: US 6,917,668 B2
(45) Date of Patent: Jul. 12, 2005

(54) RAY TRACING KERNEL CALIBRATION

(75) Inventor: Lionell K. Griffith, Solvang, CA (US)

(73) Assignee: Digitome Corporation, Davidson, NC (US)

( * ) Notice: Subject to any disclaimer, the term of this patent is extended or adjusted under 35 U.S.C. 154(b) by 0 days.

(21) Appl. No.: 10/712,956

(22) Filed: Nov. 12, 2003

(65) Prior Publication Data

US 2004/0125909 A1 Jul. 1, 2004

Related U.S. Application Data

(63) Continuation-in-part of application No. 10/687,180, filed on Oct. 15, 2003, which is a continuation-in-part of application No. 09/709,586, filed on Nov. 13, 2000, now Pat. No. 6,671,349.
(60) Provisional application No. 60/425,808, filed on Nov. 13, 2002.

(51) Int. Cl.[7] .................................................. G01B 3/00
(52) U.S. Cl. ............................. 378/163; 378/4; 378/23; 378/205; 378/207

(58) Field of Search .................................. 378/4, 21, 23, 378/162, 163, 205, 207; 382/131; 250/206.1; 356/614, 621

(56) References Cited

U.S. PATENT DOCUMENTS

| | | | | |
|---|---|---|---|---|
| 4,777,360 A | * | 10/1988 | Carner, Jr. | 250/206.1 |
| 5,051,904 A | * | 9/1991 | Griffith | 378/23 |
| 5,070,454 A | * | 12/1991 | Griffith | 378/163 |
| 5,319,550 A | * | 6/1994 | Griffith | 382/274 |

* cited by examiner

Primary Examiner—Edward J. Glick
Assistant Examiner—Chih-Cheng Glen Kao
(74) Attorney, Agent, or Firm—Fulbright & Jaworski

(57) ABSTRACT

A ray tracing kernel calibration procedure for the film simulation mode of digitized tomosynthesis in which the coordinate of the source position with respect to an energy source, e.g., x-ray radiation, is determined. Shadow images of registration markers are used to aid in computing the azimuth; computing the elevation angle; and using the elevation angle and azimuth to compute the coordinate of source position with respect to the sensor.

10 Claims, 7 Drawing Sheets

US 6,917,668 B2

RAY TRACING KERNEL CALIBRATION

CROSS REFERENCE TO RELATED APPLICATION

This application claims the benefit of Provisional Patent Application No. 60/425,808, filed Nov. 13, 2002, and is a continuation-in part of U.S. patent application Ser. No. 10/687,180 filed on Oct. 15, 2003, which in turn is a continuation-in part of U.S. patent application Ser. No. 09/709,586 filed on Nov. 13, 2000, now U.S. Pat. No. 6,671,349, as well as being a continuation-in-part of U.S. patent application Ser. No. 09/709,586 filed on Nov. 13, 2000.

FIELD OF THE INVENTION

The fields of art to which the invention pertains include the fields of dynamic tomography and computed tomography.

BACKGROUND OF THE INVENTION

A unique x-ray imaging and inspection system that combines 3D volumetric imaging and conventional 2D radiography for a complete x-ray inspection solution has been provided under the mark Digitome. For purposes of this application, the system will be referred to a "digitized tomography". Digitized tomography technology has been used for film based 3-dimensional x-ray imaging, and has been enhanced to incorporate digital flat panel x-ray detectors, resulting in examinations being made in minutes. Its features, provide unique capabilities to view any horizontal or vertical plane, scan through the volume in 0.005" increments and measure internal features. See Griffith U.S. Pat. No. 5,051,904 ("Computerized Dynamic Tomography System"), U.S. Pat. No. 5,070,454 ("Reference Marker Orientation System For A Radiographic Film-Based Computerized Tomography System"), and U.S. Pat. No. 5,319,550 ("High Resolution Digital Image Registration"), the disclosures of which are incorporated herein by reference.

The digitized tomography software contains what is known as the digitized tomography kernel. It is a set of software modules that are used to compute digitized tomography views. One defines the geometry by which the images are formed, the data arrays that contain the image data, and the coordinates of an object space. The resultant voxel value is returned to the calling software. It is the calling software's responsibility to resend the coordinates and store the voxel values so they produce the desired digitized tomography view foil.

From its inception, the digitized tomography kernel was based upon a digital simulation of what is known as the film mode. Referring to FIG. 1, its geometric derivation assumes the source 10 is at a canted angle with respect to the image plane 12. The object to examine is positioned centrally over the intersect 14 of the x-ray source optical axis 16 and the image plane. The object is then is stepwise rotated about an axis perpendicular to the image plane 12 and that passes through the above intersect. An x-ray image is acquired at each rotation position of the object.

In the film simulation mode, each acquired image is rotated by the same angle as was the object when it was exposed. The resulting images are stacked with their axes of rotation coincident. Finally, each image is translated radially inward from the axes of rotation by a distance related to the object level one desires to observe. The translation distance is a function of the perpendicular distance between the image plane and the view plane. Light passing through a stack of film positioned thusly will reveal the features at the desired view plane.

Referring to FIG. 2, an alternate geometry would be useful. For example, the x-ray optical axis 16 could be perpendicular to the image plane and the axis of rotation of the object could be at another angle with respect to the image plane 12. This would allow the instrumentation to fit into a much smaller column because the source is immediately above the energy sensor in the form of an image plate rather than offset to the side. It would also permit larger and taller objects to be examined using a given image plate than does the current geometry.

BRIEF SUMMARY OF THE INVENTION

The present invention is directed to a ray tracing kernel calibration method for digitized tomography that can be used with the currently used geometry, the alternate geometry, and potentially many other geometries, as described in the Math Model, infra and in Appendices A through G, which are incorporated herein. In an alternate geometry for operation of the digitized tomography kernel, the x-ray optical axis is perpendicular to the image plane and the axis of rotation of the object is at a canted angle with respect to the image plane. In a film mode simulation geometry, the object plane is not parallel to the film plane and the geometric magnification varies over the film plane. Marker disks and a misalignment post are used to calibrate the alternate geometry.

The film mode simulation digitized tomosynthesis kernel math is described in Appendix B. That kernel is limited to the axis of rotation of the object being perpendicular to the image plane.

The present invention provides a calibration procedure for the film simulation mode in which the coordinate of the source position with respect to an energy source, e.g., x-ray radiation, is determined. Shadow images of registration markers are used to aid in computing the azimuth; computing the elevation angle; and using the elevation angle and azimuth to compute the coordinate of source position with respect to the sensor.

More particularly, the coordinate of the source position with respect to the x-ray radiation, is determined, comprising the steps of:

placing a first registration marker that is substantially opaque to the x-ray radiation on a first location proximate the energy sensor, e.g. an image plate, and along the object's axis of rotation;

obtaining a first shadow image corresponding to the first registration marker by exposing the first registration marker to energy from the x-ray radiation source;

placing a second registration marker that is substantially opaque to the x-ray radiation on a calibration post disposing the second registration marker at location distal from the image plate spaced at a predetermined distance from the first location along the object's axis of rotation;

obtaining a second shadow image of the calibration post corresponding to the second registration marker by exposing the second registration marker to x-ray radiation from the source;

determining the distance from the source of the x-ray radiation to the image plate at the intersection of the axis with the energy sensor;

determining the height of the second marker;

determine the central coordinates of the first and second marker shadows;

computing the azimuth;

computing the elevation angle; and using the elevation angle and azimuth to compute the coordinate of source position with respect to the sensor.

The azimuth can be computed from the triangle formed by the marker centers and image axes. The elevation angle can be computed by computing an angle A as the arc tangent of (the height of the calibration post divided by the length of the shadow of the calibration post), computing an angle B as the arc sine of (the sine of angle A times the shadow of the calibration post divided by the source distance), computing an angle C as 180°−A−B, computing a distance c as the square root of $Hp^2$ plus $Ls^2-2.0 \times Hp \times Ls \times cosine(C)$, where Hp is the height of the calibration post and Ls is the length of the shadow of the calibration post, computing the height y of the source above the image plane as c×sine (A), and computing the elevation angle as arc sine of (y divided by the source distance).

Features and advantages of the invention will be described hereinafter which form the subject of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION OF THE INVENTION

Figure 1:
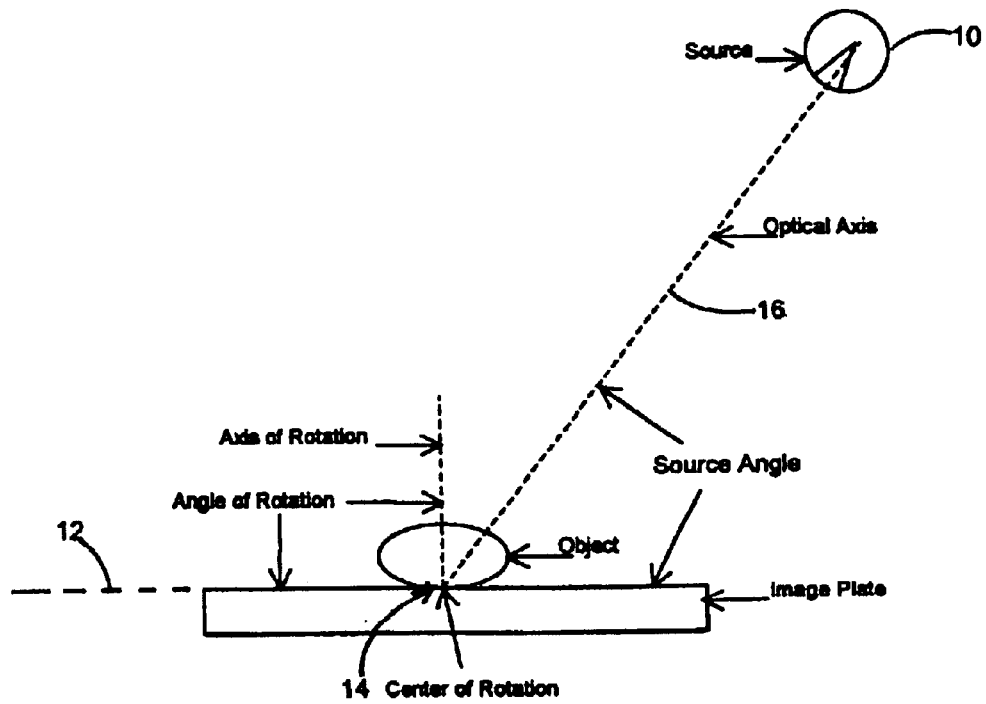
FIG. 1 is a schematic depiction of film mode operation of the digitized tomography kernel wherein the source is at a canted angle with respect to the image plane.

The underlying conventional geometry (see FIG. 1) math model assumed the source and the ray passing from the source through the center of rotation were on the plane that is perpendicular to the image plate, parallel with the long axis of the image plate, and passing through the center of rotation of the turntable. Small errors of alignment off that plane can cause significant degradation in the computed image. Appendix D offers a discussion of the calibration and correction of that misalignment error for the conventional geometry math model. There was no consideration of errors in the angle between the source to center ray and the image plate (the so called source angle). It was presumed that angle could be set "close enough" to not cause significant problems.

The ray tracing kernel requires a slightly different implementation for the misalignment correction. It also facilitates the application of corrections for the source angle. The effects of errors in the specification of source angle are small but may be significant in their impact upon dimensional measurement accuracy and 3D projections. Especially, when the errors are large or the object height is a significant fraction of the distance between the source and the center of rotation.

For the ray tracing kernel to work correctly, the position and relationship between the image plate, the object to be examined, and the source must be specified as precisely as possible. The strategy that is being proposed is to measure that which is not so critical and calibrate that which is critical.

The Coordinate System

In the conventional Digitome geometry (see FIG. 1), the X axis is left to right and parallel with the long axis of the image plate. The Y axis is vertical. The Z axis is in and out and parallel with the narrow axis of the image plate. The origin of the system is the outer left most pixel on the image plate. One coordinate increment is equal to one pixel.

The standard position of the source is on the XY plane. The source angle is equivalent to the elevation angle from ballistics. The standard alignment is equivalent to north or 0 degrees azimuth from ballistics. Elevation angle and azimuth will be the nomenclature used to describe the two angles representing the orientation of the source with respect to the image plate.

The distance between the center of rotation and the source is known as the source distance.

Calibrating Conventional Geometry

Figure 5:
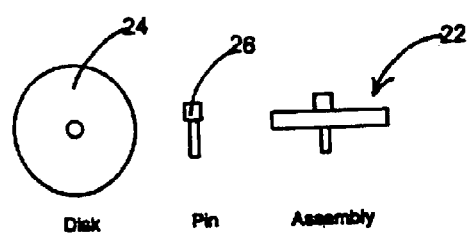
FIG. 5 depicts a marker in the existing system in which the object is a round marker disk with a central pin made of a material suitably opaque to x-rays.
Figure 6:
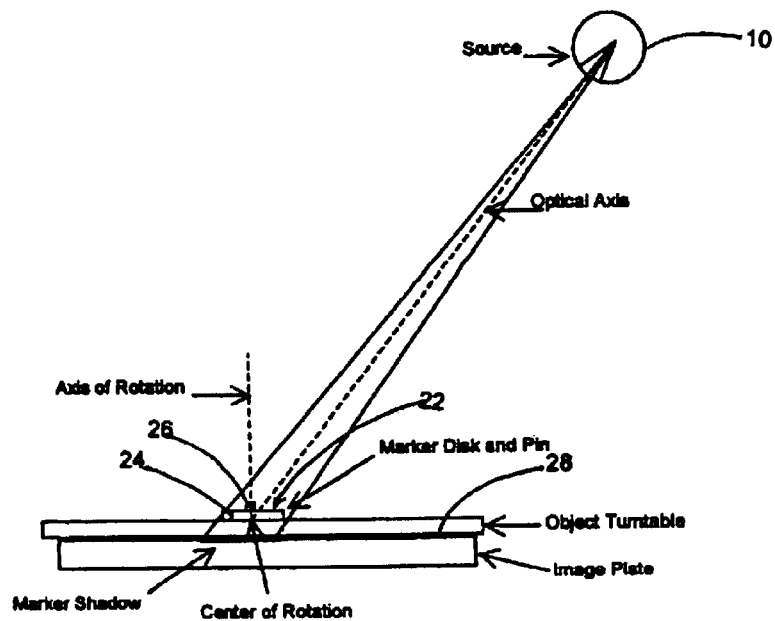
FIG. 6 depicts use of the disk and pin of FIG. 5 in a first step in calibrating the geometry of the system.

The existing system uses a two step geometry calibration. The object is a round marker disk with a central pin made of a material suitably opaque to X-rays (FIG. 5). In the first step, the disk and pin fits into the center of the object turntable (FIG. 6). An image is taken and is used to discover the coordinates of the center of rotation.

Figure 7:
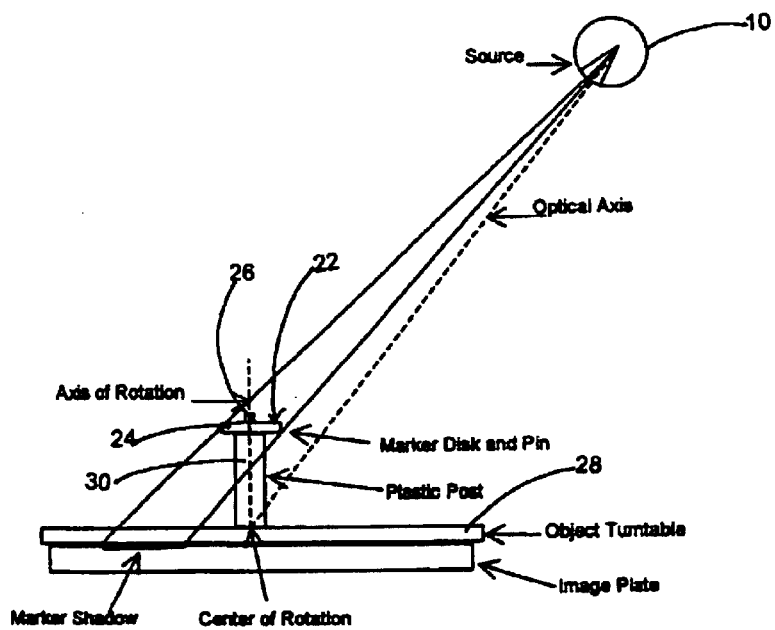
FIG. 7 depicts a plastic post with a similar pin at one end and hole to receive the pin of the round disk, inserted into the central hole of the object turntable in a second step in calibrating the geometry of the system.

In the second step, a plastic post with a similar pin at one end and hole to receive the pin of the round disk is inserted into the central hole of the object turntable. The round disk is installed in the upper hole of the plastic post (FIG. 7). A second image is taken and is used to discover the misalignment coordinate. The central coordinate of the marker shadows is measured by the graphical interactive method disclosed in an earlier technical disclosure (Appendix E).

The center coordinate, the misalignment coordinate, the length of the plastic post, source distance and the pixel size can be used to compute corrections for the source angles. The calibration technique for the misalignment angle aka azimuth angle is the subject of patent application Ser. No. 10/687,180 filed on Oct. 15, 2003, titled "Ray Tracing Kernel", extended to include the elevation angle of the source.

The center marker, the post, and a second marker in the upper position could be combined into one assembly and would require only one image to be taken. However, the sizes and angles would have to be such that the images of the two markers were distinct. If so, the usage of the marker shadow images would be identical to the two calibration image case.

The calibration process is as follows:

Length expressed in a common engineering unit—inches, millimeters, etc.

Figure 10:
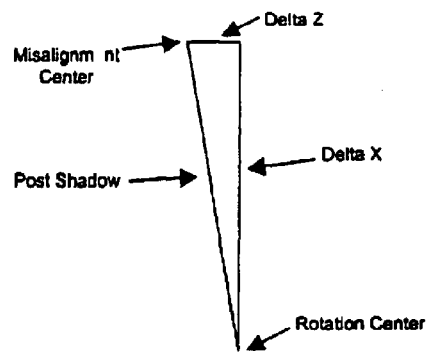
FIG. 10 is an azimuth calibration triangle formed by the marker centers and image areas.
Figure 11:
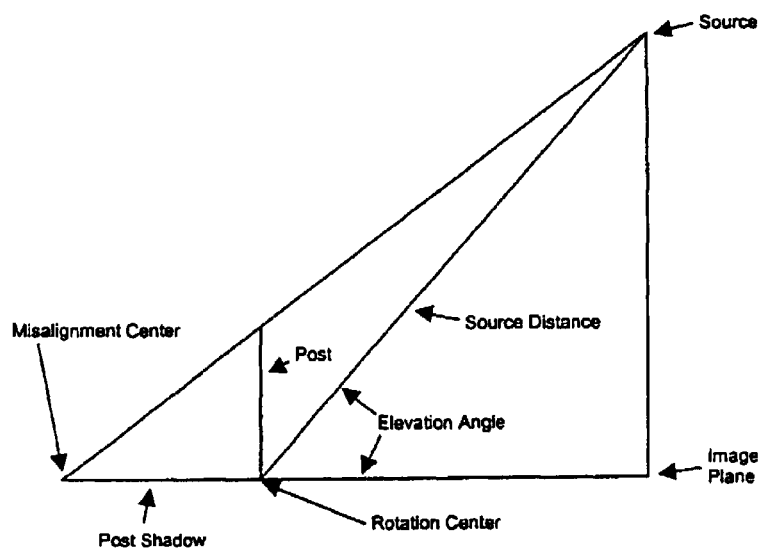
FIG. 11 is an elevation calibration triangle.

```
Coordinates expressed in unit pixels
Angles expressed in degrees
Acquire
    Pixel size
        From image plate manufacturer
    Source distance
        From center of source exit window to the center of rotation
        Can be measured with a simple tape measure
        One inch error in results in approximately 0.1 degrees error in
        elevation angle
    Height of misalignment post plus top marker (plus bottom marker if
    combined)
        Should be measured as accurately as reasonably possible
        Micrometer caliper is likely accurate enough
        The goal is a good bit less than a one pixel size error
    Coordinates of the marker centers
        Expose individual or combined markers
        Determine central coordinates of marker shadows
        Use method suggested in Appendix E
Compute Azimuth
    Referring to Figure 10, consider the triangle formed by the marker
    centers and image axes
    Delta X = (misalignment X − center X) × pixel size
    Delta Z = (misalignment Z − center Z) × pixel size
    Post shadow length = SQRT(delta X ² + delta Z ²)
    If post shadow length NOT Zero AND delta Z NOT Zero
        azimuth angle = − arc sine (delta Z/post shadow length)
    Else azimuth angle = 0.0
    If delta X LESS THAN Zero AND delta Z GREATER THAN Zero
        azimuth angle = azimuth angle + 360.0
    Else if delta X GREATER THAN Zero
        azimuth angle = 180.0 − azimuth angle
Compute elevation angle
    Referring to Figure 11, consider the triangle formed by
        The source
```

-continued

```
        The rotation center
        The misalignment center
            As shadow of top of calibration post
        Compute angle (source, misalignment center, rotation center)
            A = arc tangent (post height/post shadow length)
        Compute angle (misalignment center, source, rotation center)
            By law of sines (see Appendix E)
            B = arc sine (sine (A) × post shadow length/source
            distance);
        Compute angle (misalignment center, rotation center, source)
            C = 180° − A − B
        Compute distance (misalignment center, source)
            By law of cosines (see Appendix E)
            c = square root (post height ² + post shadow length ² −
            2.0 × post height × post shadow length × cosine (C))
        Compute height of source above image plane
            y = c × sine (A);
        Compute elevation angle
            elevation angle = arc sine (y/source distance)
Compute coordinate of source position with respect to image plate
        Using standard 3D Coordinate Transformation Matrix; see
        Appendix F ("Basic 3D Math") and Appendix G ("Matrices")
        Set coordinate
            X = 0.0
            Y = source distance/pixel size
            Z = 0.0
        Rotate about the Z axis
            angle = 90° − elevation angle
        Rotate about the Y axis
            angle = azimuth
        Translate
            X = center X
            Y = 0.0
            Z = center Z
```

There are three limiting conditions in the above ray tracing calibration method. The first is at a source elevation angle of 90 degrees. At 90 degrees elevation, the source is exactly overhead the reference position, i.e., center of rotation. Under that condition, the computed azimuth is meaningless. It makes no difference in the resultant image no matter how the source is rotated. A 90 degree elevation angle would produce correct results no matter what the azimuth. The second condition is that the closer the elevation angle is to 90 degrees, the greater the error in computing azimuth with a fixed calibration post height. For example at an elevation angle near 45 degrees, a post height of approximately 3 inches is adequate. For an elevation angle of 70 degrees, a calibration post height of 5 inches is required to get similar quality results. The problem arises from the small inaccuracies of measuring the centers of the marker shadows. In one study it was determined that center measurements have a standard deviation of 0.16 pixel. The third condition is at a source elevation angle such that the source is at or below the calibration post height above the image plane. Under that condition, the computed elevation angle and azimuth are meaningless. The reason is that the ray passing through the top of the calibration post is either parallel to the image plane or divergent upward from it. Thus there can be no shadow in any possible image of the top calibration marker. Thus making calibration impossible under those conditions. However, it is quite doubtful that the third limit will be encountered in any real system. For example, using a calibration post that's 5 inches tall, placing the source at 7.005 degrees would require an image plate that is more than 32 miles wide—assuming the current 0.005 inch pixel. The recommended value for elevation angle is between 30 and 70 degrees. Care must be exercised when going beyond those limits.

Although the present invention and its advantages have been described in detail, it should be understood that various changes, substitutions and alterations can be made herein without departing from the spirit and scope of the invention. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the invention is intended to include within its scope such processes, machines, manufacture, compositions of matter, means, methods, or steps.

Math Model

Figure 3:
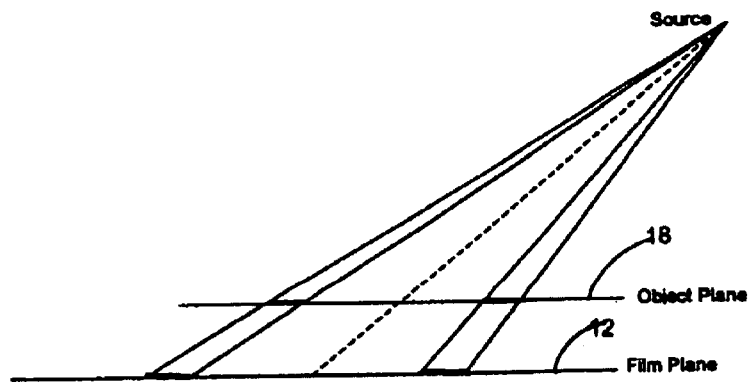
FIG. 3 is a schematic representation of a film mode simulation geometry wherein the object plane is parallel to the film plane and the geometric magnification projects uniform shadows of the features of the object plane.

The film mode simulation geometry works in the film mode because the object plane is parallel to the film plane. Referring to FIG. 3, the geometry is such that the geometric magnification of projected shadows of the features of the object plane 18 is uniform. Thus the appropriate superposition of the film images places the projected shadows of the features of the view image plane in coincidence.

Figure 4:
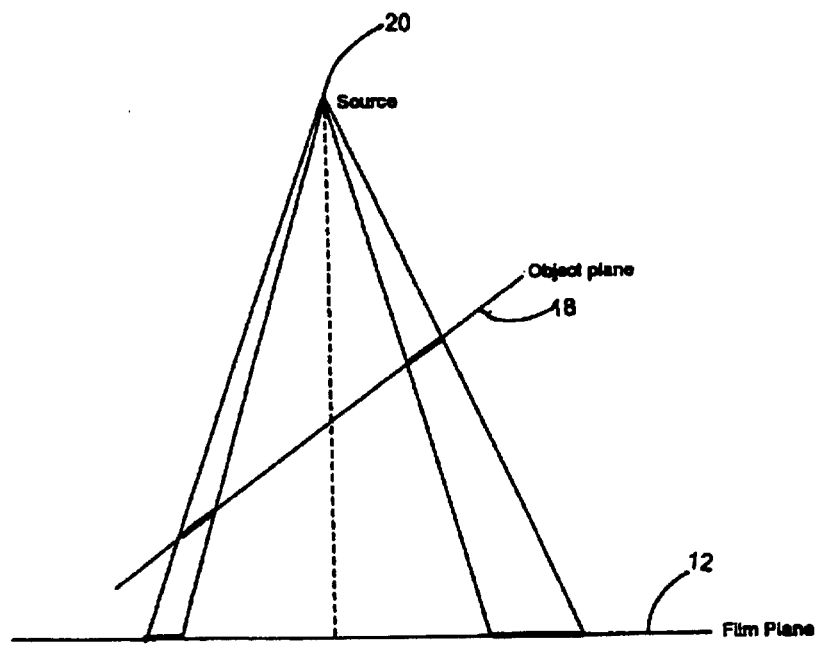
FIG. 4 is a schematic representation of an alternative geometry wherein the object plane is not parallel to the film plane and the geometric magnification varies over the film plane.

Referring to FIG. 4, in the alternate geometry, the object plane 18 is not parallel to the film plane and thus the geometric magnification varies over the film plane. Since the film is dimensionally fixed, it is therefore not possible to superposition the film so that the projected shadows of the features of the object plane are in coincidence. In order to form an image by combining alternate geometry projections, one must accommodate the variation of magnification.

If one specifies the geometry of image formation sufficiently, one can mathematically trace a ray from the source 20, through the object space voxel to the image plane and compute the coordinate of the shadow of the voxel on the image plane. If done for each object rotation, the image data could be extracted and combined to form the estimate of the given object space voxel. Since the ray tracing process includes the geometric magnification effects, both the current and alternate geometries are applicable, as are many other geometries. The geometry can be specified with sufficient accuracy and precision to achieve acceptable results.

Limits to Resolution

There are three primary factors limiting resolution.

The first limitation is the spot size of the x-ray source 20. Each edge of the projected image has a penumbra caused by that spot size. Its dimension is the spot size times the distance between the object feature and the image plane divided by the distance between source 20 and the image plane. Since the usual spot size is in the order of a millimeter, the source distance in the order of a meter, and the feature distance is in the order of a few tens of millimeters, the penumbra is in the order of a few tens of thousandths of a millimeter or a few thousandths of an inch. The alternate geometry may have larger penumbra due to the larger distances between the object feature and the image plane. Using a smaller spot size and/or longer source distances can reduce this effect.

The second limitation is the pixel size of the image plate. Since we use data from eight or more images, its possible to obtain resolutions better than the pixel size of the image plate. Use of multiple images also tends to cancel a portion of the penumbra effect.

The third limitation is the specification of the geometry. Errors in the specification of the position of the source 20 have an effect similar in magnitude as the penumbra effect. Those errors are attenuated by the ratio of the source distance to feature distance. Errors in the identification of the center of rotation has a one to one impact. Errors in specification of the various angles are dependent upon the distance over which the error is communicated. Acceptable errors for the current image plate are in the order of a few hundredths of a degree.

With such tight tolerance of angles and dimensions, the geometry must be either very carefully measured or calibrated by using the system and specially constructed objects.

Specifying the Geometry

Figure 2:
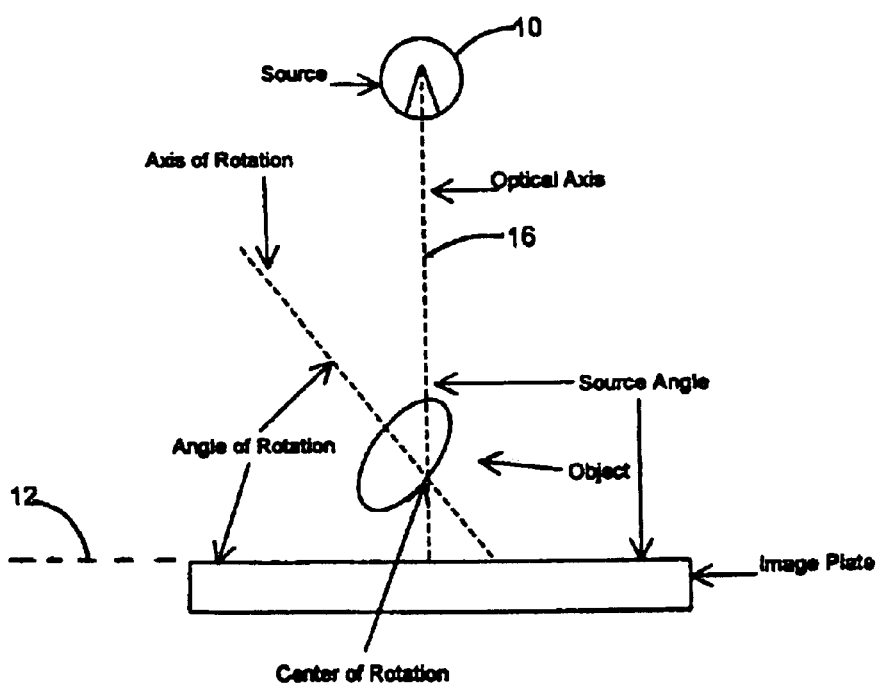
FIG. 2 is a schematic depiction of an alternate geometry for operation of the digitized tomography kernel wherein the x-ray optical axis is perpendicular to the image plane and the axis of rotation of the object is at a canted angle with respect to the image plane.

The assumption is that there is a fixed relationship between the source 20 and image plate, that the object is between the source 20 and the image plate, and that it is the object that is rotated about a fixed axes between each exposure cycle. This restriction can be removed by measuring the precise location and orientation of the source 20, the object, and image plate. However, since the goal is to achieve a working system within the bounds of currently available technology, the above restrictions are necessary. Relatively simple input transformations can be used, if required, to adapt to precise and accurate location and orientation measurements The Coordinate System Looking at the system as it is presented in FIGS. 1 and 2, the X axis is left to right, the Y axis is vertical, and the Z axis is in and out. The origin of the system is the outer left most pixel on the image plate. One coordinate increment is equal to one pixel. This makes the image plate coincident with the X,Z plane. The X,Z plane in the new coordinate system is the same as the X,Y plane of the original system. The change is necessitated by the three dimensional (3D) math required by the alternate geometries. The original geometry only required two dimensional (2D) math.

Dimensions to Specify

1. The source to image plate distance (Source Distance)
2. The image plate dimensions (Width in Z axis, Height in X axis)
3. The image plate pixel size (From vendor)
4. The center of rotation to image plate distance (Object Distance)
5. The object radius of interest (From operator)

The source to image plate distance is not critical. Errors are diminished by the ratio of the feature to image plate distance to the source to image plate distance.

The image plate dimensions and pixel size are given by the manufacturer.

The center of rotation to image plate distance is also not critical. Its used to compute the object plane level offset so that one can specify the view level as distance from the base of the object.

The object radius of interest is perhaps the least critical. It simply sets the computed image size. It is necessary that it is sufficient to include the features of interest but not so large as to unnecessarily extent the computation time.

Angles to Specify

1. The source to image plate plane angle in the YZ and XZ planes (Source Angle)
2. The object axis of rotation to image plate plane angle in the YZ and XZ planes (Object Angle)
3. Rotation angle of object for each image (Rotation Angle)

In accordance with this invention, one defines, by manufacture and/or by measuring the source to image plate plane angles and the object axes of rotation to image plate plane angle as closely as reasonably possible. Small errors can be measured using the system and specially constructed objects and corrections can be computed. If the manufacture or measurement is precise and accurate enough, corrections won't be required, in which case the ray tracing method is not limited to any particular geometries.

It is apparent from our current system that the manufacture of the means to set the rotation angle of the object is sufficiently precise and accurate for the existing image plate.

Calibrating the Geometry

The existing system uses a two step geometry calibration. Referring to FIG. 5, the object 22 is a round marker disk 24 with a central pin 26 made of a material suitably opaque to x-rays.

Referring to FIG. 6, in the first step, the disk 24 is retained on the object turntable 28 via insertion of the bottom of the pin 26 through the disk 24 and into a hole in the center of the object turntable 28. An image is taken and is used to discover the coordinates of the center of rotation. In the alternate geometry, it is used in the same manner Referring to FIG. 7, in the second step, a plastic post 30 carries the marker disk and pin assembly at its top end. The plastic post 30 has a similar pin at its bottom end, inserted into the central hole of the object turntable 28, and a hole at its upper end to receive the bottom of the pin 26 through the round disk 24. A second image is taken and is used to discover the misalignment coordinate. The central coordinate of the marker shadows is measured by the graphical interactive method, described in Appendix C.

Figure 8:
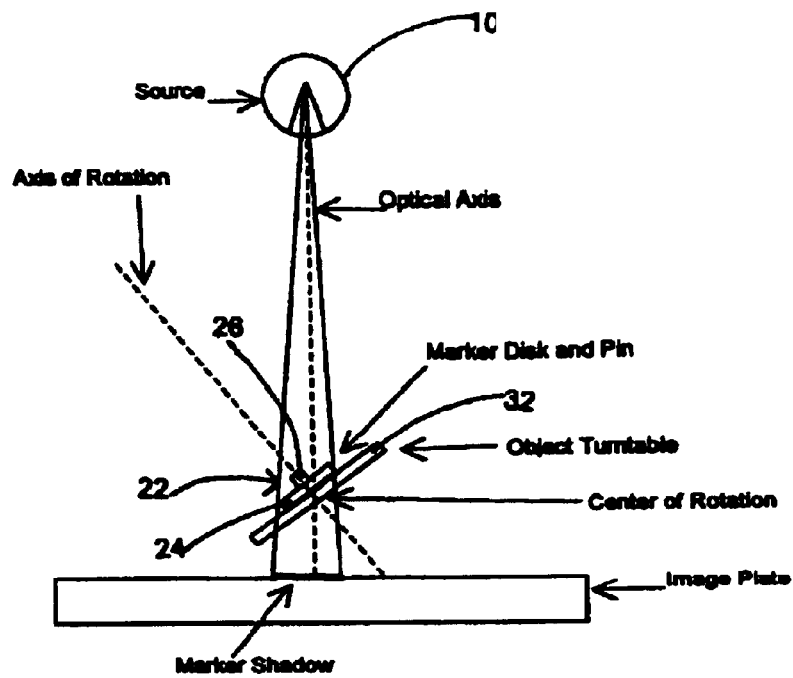
FIG. 8 depicts one method by which the marker disk and misalignment post are placed to calibrate the alternate geometry.
Figure 9:
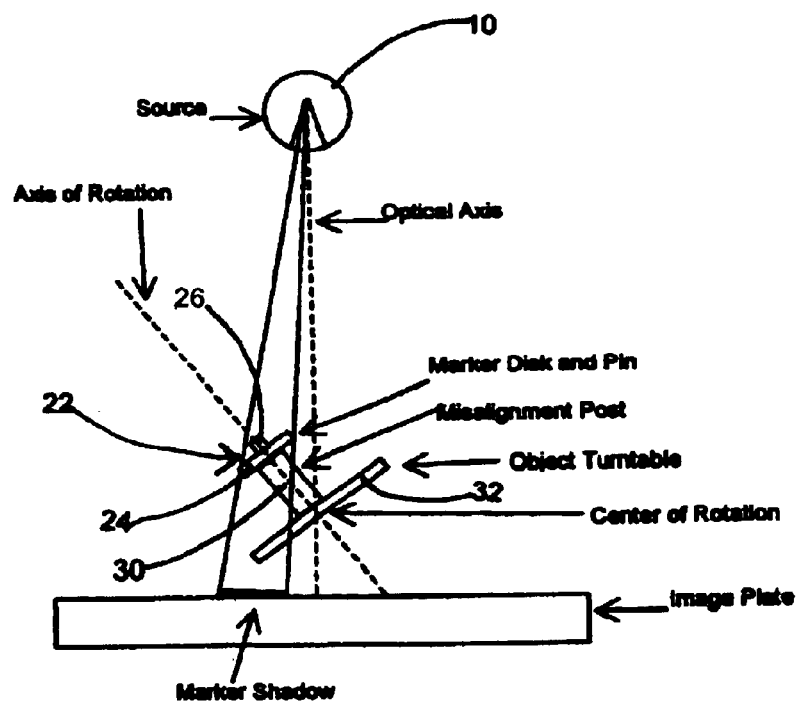
FIG. 9 depicts another method by which the marker disk and misalignment post are placed to calibrate the alternate geometry.

The center coordinate, the misalignment coordinate, the length of the plastic post 30, and the pixel size are used to compute corrections for the source and object angles. This calibration technique is the subject of my U.S. patent application Ser. No. 09/709,586, filed Nov. 13, 2000, entitled "Tomosynthesis System and Registration Method," hereby incorporated herein by reference. However, it was not then extended to the alternate geometry. FIGS. 8 and 9 indicate how the marker disk 24 and misalignment post can be placed on an angled object turntable 32 to calibrate the alternate geometry.

Axial Misalignment Calibration

The digitized tomography process requires very precise image registration for it to produce high quality computed images. The requirement is such that every pixel in every source image must be known to the process to within a fraction of a pixel. A method that provides for such high resolution image registration of film x-ray images consists of a fixture, a setup process, and calibration procedure that assures a very specific geometry of exposure and allows each digitized film image to be transformed into a standard registration and format. Because the x-ray source is position immediately overhead the center of rotation of the fixture and the fixture is tilted to the desired angle that axial misalignment of the x-ray images is not encountered.

The current digitized tomography calculations assume the path between the center of the x-ray source and the center of rotation of the non-film fixture's turntable 28 falls on a plane that is perpendicular to the non-film image plate's surface, parallel to the long axis (the "Y" axis) of the non-film image plate, and passes through the center of rotation of the fixture's turntable 28. Since the current fixture is placed horizontally and the x-ray source is moved to the side and angled toward the center of rotation, an axial misalignment is possible without using special alignment procedures and tools. Even a small misalignment can cause serious degradation of the resultant computed digitized tomography views.

Currently, the center of rotation is calibrated using an image of a circular marker placed at the center of rotation in a manner identical to the method used to identify the center of rotation of film images. Because all images can be taken with an identical registration, the three reference mark technique used with film images is not required. However, a second reference mark must be used to measure the axial misalignment of the x-ray optical axis. That marker may be of the same size and material as the center reverence mark but must be displace above the center of rotation by some distance. Since the center position of the marker can be determined to approximately ½ a pixel width, that distance need only be approximately ½ the maximum possible image radius. The current image plate is 2304 pixels wide with a 200 pixel "gutter" along one edge. That makes the effective radius (2304−200)/2=1145 pixels at 0.005 inches per pixel, that is, 5.724 inches. One half of that is 2.86 inches.

Using the center coordinates of the two reference markers, the axial misalignment angle can be determined and a correction to the digitized tomography calculations can be applied to the "X" and "Y" axis displacement values. The process is as follows:

Let x1,y1 be the pixel coordinate of the center of the center reference mark image. Let x2,y2 be the pixel coordinate of the center of the elevated center reference mark image. Let the x-ray optical axis be more or less parallel to the "Y" axis in the positive direction. The distance between centers of the reference marks is computed by taking the square root of the sum of the squares of the differences between the first and second coordinates: distance=sqrt((x1−x2)*(x1−x2)+(y1−y2)"(y1−y2)). That distance is divided into the differences between the coordinates to compute the sine and cosine of the misalignment angle: sine of misalignment angle=(x2−x1)/distance and cosine of misalignment angle=(y2−y1)/distance.

The Displacement is the normally calculated displacement value and is computed as a function of the image level. The "X" axis displacement value is computed as the Displacement times the sine of the misalignment angle and the "Y" axis displacement value is computed as the Displacement times the cosine of the misalignment angle. The adjusted displacements are applied to their respective axis calculations as described elsewhere. A procedure similar to the one used with the film mode simulation geometry can be used to compute and apply the corrections to the alternate geometry.

An additional calibration step can be applied to the alternate geometry—the distance between the image plate and the center of rotation (object distance). Errors in that dimension can affect the accuracy of measurement of feature size, although simple measurement should be enough because the effect of that error is the size of error divided by the source distance. One way to calibrate that dimension is to place two marker disk 24 and pin 26 assemblies a known distance apart on the object turntable 32, centered on the center of the turntable 32 and oriented so the line connecting the centers of the disks is parallel to the Z axes. The following relationship are true:

Solving for the object distance gives a calibrated estimate of the required dimension.

---

Ray Tracing Process

1. Compute alignment calibration angles
a.   Acquire centroid of center calibration marker shadow in image plane
    i.      Coordinate is X1a,Z1a by method in Appendix C
    ii.     Note: the image plane is parallel with the XZ plane -continued Ray Tracing Process iii. Note: the origin of the image plane is at the coordinate system origin
 b. Acquire centroid of misalignment calibration marker shadow in image plane
  i. Coordinate is X1b,Z1b by method in Appendix C
  ii. Note: if Z1a equals Z1b there is no misalignment
 c. Compute misalignment angle in XZ plane
  i. Misalignment angle equals arctan((X1b-X1a)/(z1b-z1a))-90°
 d. Compute angle in XY plane
  i. Convert height of misalignment calibration post to pixel units
  ii. Source angle equals arctan((misalignment post height)/(X1b-X1a))
  iii. For current geometry, angle is source angle
   1. Object angle is 0°
   2. Presumes accurate construction
   3. Implies object plane is parallel to image plane
   4. Construction and calibration procedure seems adequate
  iv. For alternate geometry, angle is object angle
   1. Source angle is 90°
   2. Presumes accurate alignment of image plane to source path
   3. Implies optical axis is normal to image plane
  2. Compute corrected 3D coordinates of source
 a. Transform source distance to pixel units
 b. Xs = X1a
 c. Ys = (source distance) × sin(source angle)
 d. Zs = Z1a
  3. Compute equation of image plate plane
 a. Vector 1 = (0,0,0),(0,(image width −1 ),0)
  i. Vx1 = 0
  ii. Vy1 = image width −1
  iii. Vz1 = 0
  iv. M1 = sqrt(Vx1^2+Vy1^2+Vz1^2)
 b. Vector 2 = (0,0.0),(0,(image height −1),0)
  i. Vx2 = 0
  ii. Vy2 = image height −1
  iii. Vz2 = 0
  iv. MZ = sqrt(Vx2^2 + Vy2^2 + Vz2^2)
 c. Normal Vector = the normalized cross product of Vector 1 and Vector 2
  i. Non-normalized vector
   1. NVx = (Vy1 × Vx2) − (Vx1 × Vy2)
   2. NVy = (Vz1 × Vx2) − (Vx1 × Vz2)
   3. NVz = (Vx1 × Vy2) − (Vy1 × Vx2)
   4. NM = sqrt(NVx^2+NVy^2+NVz^2)
  ii. Normalized vector
   1. NVx = NVx/NM
   2. NVy = NVy/NM
   3. NVz = NVz/NM
 d. Plane coefficient
  i. D = -NVx × Vx1 − Nvy × Vy1 − NVz × Vz1
  4. For each object voxel in desired digitized tomography view foil
 a. Compute 3D coordinates of object voxel
  i. Transform engineering units coordinate to pixel unit coordinate
  ii. Two dimensional coordinate transformations in XZ plane
   1. Rotate about axis of rotation to misalignment angle
   2. Rotate about axis of rotation to incremental angle
  iii. For alternate geometry
   1. Two dimensional coordinate transformation in XY plane
    a. Rotate about center of rotation to object angle
    b. Translate to the center of rotation
 b. Use results of 1 and 4a to create a 3D line
  i. (Xs,Ys,Zs),(Xo,Yo,Zo)
 c. Use results of 3 and 4b to compute intercept coordinates
  i. Dx = X − Xs;
  ii. Dy = Yo − Ys;
  iii. Dz = Zo − Zs;
  IV. mu = −(D + NVx × Xd + Nvy × Yd + NVz * Zd)/(NVx × Dx + Nvy × Dy + NVz × Dz)
  v. Xi = Xs + mu × Dx
  vi. Yi = Ys + mu × Dy
  vii. Zi = Zs + mu × Dz
 d. For each image
  i. Use results of 4c to extract projected ray pixel value
   1. Method in Appendix B
 e. Combine pixel values from 4d by method in Appendix A
 f. Store result of 4e in destination digitized tomography view data matrix.

Although the present invention and its advantages have been described in detail, it should be understood that various changes, substitutions and alterations can be made herein without departing from the spirit and scope of the invention. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the invention is intended to include within its scope such processes, machines, manufacture, compositions of matter, means, methods, or steps.

Appendix A—Variable Absorption Digital Image Combination

Review of Absorption Digital Image Combination:

The process of producing a Computed Tomographic View from multiple digitized x-ray images requires the combination of the registered pixels from each of the digitized images. The usual method used is a simple summation or averaging of the pixels to be combined. This method results in an image containing many confusing artifacts and visual blurring.

The original absorption model for combining eight images is as follows:

The minimum pixel value was assigned a transmission fraction of 0.5
  The maximum pixel value was assigned a transmission fraction of 1.0
  All other pixel values were assigned a transmission fraction proportionately between 0.5 and 1.0
  For each pixel location in the computed view
  Start with a maximum pixel value
  Successively multiply initial pixel value by the transmission fraction of that same pixel location in each of the eight images This can be accomplished using integer arithmetic as follows:

Combined pixel=Maximum pixel value
  For each of eight images in succession
   Image pixel=Image pixel+Maximum pixel value
   Image pixel=Image pixel DIV 2
   Image pixel=Image pixel−Maximum pixel value
   Image pixel=Image pixel*Combined pixel
   Image pixel=Image pixel DIV Maximum pixel value
   Combined pixel=Combined pixel+Image pixel
  Note: While floating point arithmetic could be used, integer arithmetic is much faster on most computers
  Note: While eight images were used in the present case, the method could be adapted to other numbers of images Variable Absorption Digital Image Combination:

While the fixed absorption model gave generally good results, it was thought that other values of absorption might give improved results for some examinations. For example, examinations of very dense objects might benefit from higher absorptions while examinations with low density areas of interest might benefit from lower absorptions.

The fixed absorption model has been modified to allow variable absorption using integer arithmetic as follows:

Combined pixel=Maximum pixel value

For each of eight images in succession

Image pixel=Image pixel+Maximum pixel value

Image pixel=Image pixel DIV 2

Image pixel=Image pixel−Maximum pixel value

Image pixel=Image pixel*Combined pixel

Image pixel=Image pixel DIV Maximum pixel value

Image pixel=Image pixel*Scaled absorption fraction

Image pixel=Image pixel DIV Scaling factor

Combined pixel=Combined pixel+Image pixel

Note: While floating point arithmetic could be used, integer arithmetic is much faster on most computers.

Note: While eight images were used in the present case, the method could be adapted to other numbers of images.

If the absorption fraction is one, the results are as before. Given an absorption fraction greater than one, the effect is to increase the absorption. While, an absorption fraction less than one results in a decrease of absorption effect. Visual results are as expected.

Appendix B—High Resolution Digital Image Manipulation

Review of Between Pixel Value Calculation:

A digitized image is a rectilinear matrix of numbers. Each number represents the integral intensity of a small area of the original object, picture, or transparency. In order to transform the matrix to an image the eye can use, hardware must be provided such that each number can be presented as a small area of light or dark on a video display or printing device.

When the eye looks at a small area of light, a perception of brightness results from an integration of area and intensity. That is a small area of bright will look as bright as a slightly larger area of slightly less brightness. This understanding lead to the following method of determining the value of a pixel whose coordinate fell between pixels.

Given:

A two dimensional matrix of pixel values for a source image

A fractional coordinate of a pixel value to determine
coordinate=x.fx,y.fy
Where:
x,y=the integral coordinate
fx=the fractional x coordinate
fy=the fractional y coordinate There are four nearest pixels in the source image Upper left=x,y Upper right=x+1,y Lower left=x,y+1

Lower right=x+1,y+1

There are four areas joining at x.fx,y.fy which are proportional to

=>Upper left=fx*fy*Aspect ratio

=>Upper right=(1−fx)*fy*Aspect ratio

=>Lower left=fx*(1−fy*Aspect ratio)

=>Lower right=(1−fx)*(1−fy*Aspect ratio)

Where:

Aspect ratio=y pixel resolution/x pixel resolution

It was concluded that the eye will weight the four nearest pixels proportional to the opposing areas Between pixel value=
(Upper left value*Lower right area+
Upper right value*Lower left area+
Lower left value*Upper right area+
Lower right value*Upper left area)/Aspect ratio Applications of Between Pixel Value Calculation:

The between pixel value calculation is currently used for two applications in the DT33 and DT36 programs:

Rotation and translation of digitized images

Forming the measure feature profile line

Tests have been performed yielding very good results for two more applications:

Digitized image magnification

Extended high resolution reference mark find

Several additional applications should be quite possible but are as yet untested:

Variable image area selection

Calculation of arbitrary z-axis view

Correction of digital image distortion
Magnification
Aspect ratio
Non-linear distortion Review of Rotation and Translation of Digitized Images:

The digitized images must be rotated and translated for two reasons:

1 The acquired image must be rotated and translated to a standard reference rotation and position.

2 The set of images for an examination must be rotated and translated so that the image combination will yield the computerized tomographic view at the desired level.

Given:

A two dimensional matrix of pixel values for a source image

A two dimensional matrix of pixel value locations for a destination image

A coordinate of the image center of rotation

A reference coordinate for the image center of rotation

An angle to rotate about the image center of rotation

An x displacement of the image center of rotation

An y displacement of the image center of rotation

Transform each integral coordinate in the destination image into a fractional coordinate in the source image:

x.fx=(x destination−source center x−x displacement) COS(rotation angle)+(y destination−source center y+y displacement) SIN(rotation angle)−(2.0*source center x−reference x)

y.fy=(x destination−source center x−x displacement) SIN(rotation angle)+(y destination−source center y+y displacement) COS(rotation angle)+(2.0*source center y−reference y)

Compute the between pixel value in the source image at x.fx,y.fy and place it in the destination pixel location x destination,y destination.

Review of Forming the Measure Feature Profile Line:

The operator selects two points on the image which are the ends of a line passing through the feature of interest.

Given the coordinates of the two points x1, y1 and x2, y2
Compute the slope of the given line:

IF $x1 <> x2$ THEN slope=$(y2-y1)/(x2-x1)$

ELSE slope=sign of $(y2-y1)1E20$ or similar large number

Compute the intercept of the given line:

intercept=$y1$-slope*$x1$

For each one pixel distance between the two points on the line compute the fractional coordinate:
Compute:

x increment=$SQRT\ (1/(1+SQR(\text{slope})))$ y increment=slope*x increment x.fx=$x1$+x increment*number of pixels from $x1, y1$ y.fy=$y1$+y increment*number of pixels from $x1, y1$ For each fractional coordinate compute the between pixel value to be the corresponding feature profile line pixel value.

Digitized Image Magnification:

Previous applications were based upon the fractional coordinates being one image pixel apart. If the fractional coordinates are spaced closer than one pixel apart the destination image is effectively magnified. That is if they are ½ pixel apart the effective magnification is 2×; ¼ pixel apart is 4× and so on.

When such a magnification is done the result is a smooth magnification of the digitized image-that appears much like the image produced by a magnifying glass. The customary approach to the magnification of a digital image is the simple square replication of each pixel. That is for a 2× magnification each pixel is replicated into a 2 by 2 square. The resulting image appears magnified but has a square tile effect which reduces the eyes ability to see the shape of the magnified features.

Magnification of digital images is becoming more important as the resolution of image digitizers and digital display devices improves. Current resolution is such that it is difficult to see features that are a few pixels in size. This trend is expected to continue.

Extended High Resolution Reference Mark Find:

The current method of locating the center of the registration reference marks is as follows:

The operator points to the inside of the reference mark.

The computer scans on the x and y axis until it finds a maximum in the slope of the image intensity higher than the noise peaks.

The fractional coordinates of the maximum slope is determined.

The position of the maximum is determined by using the maximum slope along with the preceding and following slope values to form a second order curve.

The position of the maxima of the second order curve is assumed to be the position of the edge.

The trial center of the mark is then computed as the mean x,y coordinate.

The computer then takes the trial center and similarly computes a second trial center.

The compute then takes the second trial center and computes the final center coordinate.

Since the reference marks are ellipsoidal:

The center coordinate of both reference marks are determined.

The errors in angle and position are computed.

The rotation and position of the image is adjusted by the rotation and translation procedure.

The computer then determines the new center coordinates of the reference marks.

The sequence is repeated until the errors in angle and position are reduced below a small amount.

An extended method is as follows:

The operator points to the inside of the reference mark.

The computer scans on the x and y axis until it finds a maximum in the slope of the image intensity higher than the noise peaks.

The fractional coordinates of the maximum slope is determined.

The position of the maximum is determined by using the maximum slope along with the preceding and following slope values to form a second order curve.

The position of the maxima of the second order curve is assumed to be the position of the edge.

The trial center of the mark is then computed as the mean x,y coordinate.

The computer then takes the trial center and similarly computes a second trial center.

The compute then takes the second trial center and computes the final center coordinate.

Do the above for both reference marks.

Compute the angle and positional error.

Use the same method used to create a feature profile line to produce an x,y scan across the reference marks whose angle is adjusted for the angular error found above.

In a similar manner find the fractional coordinates of the maximum slope in the pixel intensity.

Compute the center coordinates for both reference marks as the mean coordinate of each.

Compute a revised angle and position error.

Repeat the second process until the computed angle and position error changes less than some small amount.

The advantage of this extended method is that the true error in angle and position of the image is determined without the time consuming multiple rotation and translation adjustment. This becomes vary important as the resolution of the digitized image improves. Current images are 3.1 meg pixels with a possible 12.6 meg pixels soon. The higher resolution image will take too much time and memory to allow such adjustment.

Variable Image Area Selection:

The current method of image area selection is as follows:

The image is adjusted to standard position and rotation.

The operator selects a packing fraction 1 to 1 4 to 1 9 to 1 16 to 1.

The central area of the source image is packed into the destination image area.

This method has several problems:

The time and memory required to adjust the digitized image to standard position and rotation.

The inflexibility of the integral pixel packing approach not allowing optimum sizing of the area of interest after digitization.

Demagnification of the digitized image should be possible in a manner vary similar to the magnification discussed above. Compute the fractional coordinates so that they are more than a source pixel apart. Any arbitrary demagnification should be able to be achieved.

Rotation and translation can be accomplished at the same time by using the extended reference mark find method coupled with the coordinate transformation procedure above. Thus the excessive time and memory required for the current method can be eliminated along with allowing an optimum selection of the area of interest.

Calculation of Arbitrary Z-axis View:

The current method of computation of a z-axis view is limited to any x or y line in the currently formed computed tomography view series. A specific x or y line is taken from each stored computed tomographic view and displayed side by side. This is not quite satisfactory because:

The entire series must be created first

Too much time is taken read all of the data from the disk

The feature of interest may not be along the x or y axis

The feature of interest may in fact be curved

An alternative is:

The operator selects an arbitrary path on one view.

A list of fractional coordinates one pixel apart are generated from that path or possibly magnified or demagnified as required.

Transform that list so that the appropriate rotations and translations are included.

Acquire pixel data along that transformed path by the above between pixel method.

Combine the pixels by the currently used absorption method.

Present the computed paths side by side.

Correction of Digital Image Distortion:

If an array of fractional coordinates can be computed to correct for the distortion in a digital image, the above between pixel calculation can be used to correct that distortion. Thus linear distortion such as magnification or aspect ratio can be corrected with ease. Non-linear distortion such as that resulting from a variable speed scanning camera can be corrected if that non-linearity were adequately known.

Appendix C—High Resolution Registration of Digital Images

The coordinate system to be used in this disclosure is as follows:

The film is placed at the image plane

The image plane is the x,y plane

The image plane is tilted at some angle with respect to a base plane

The y axis is parallel to be base plane

The image is formed by x-rays projecting a shadow of an object at or near the image plane Multiple images are formed by rotating the object about an axis of rotation The z axis is parallel to the axis of rotation The intersect of the axis of rotation and the image plane is the center of rotation The center of rotation is the desired origin of the coordinate system Previous disclosures described a method of using reference marks to transfer the registration of the object to the computer. Several methods of locating and using the centers of those markers were discussed.

As the image resolution is pushed to higher levels, registration becomes a more demanding problem to be solved. For digitized tomography brand Computerized Tomography to work at its best, the multiple digitized images must be in registration to within a pixel.

After digitization of the x-ray images, the two registration marks centers are located, the apparent center of rotation is computed based upon a previously established relationship between the registrations marks and the center of rotation. The image is then moved to a standard position and rotation:

The line joining the centers of the registration marks is parallel to the y axis.

The center of rotation is positioned at the center of the digital image.

Since the acquired images must be rotated to form the final CT view, the quality of the result is vary sensitive to variations in registration along the y axis. This is especially true as the area of interest is more distant from the center of rotation.

When working with pixels as small as a few mills, the projected image of the reference marks becomes an ellipse rather than a circle. Center find routines based upon the assumption of a circle fail to locate the center of the mark to within the required fraction of a pixel. In fact, variations in the position of the final image of more than five pixels, have been observed.

Methods have been developed that markedly reduces this problem.

Review of Previously Disclosed Center Find Methods:

First Attempt—No Longer In Use:

Step Description

1 Locate the coordinates of all reference mark edge pixels

2 Compute mean x and y coordinate

3 Use computed x,y coordinate as center of reference mark

Method One—In Use:

Step Description

1 Use mouse to point to inside of reference mark

2 Use pointed to pixel as starting point

3 Scan along the x axis to find maxima or minima of differential of pixel level

4 Compute x coordinate of left and right edge of reference mark as position of maxima or minima of differential 5 Compute mean x coordinate 6 Scan along the y axis to find maxima or minima of differential of pixel level 7 Compute y coordinate of top and bottom edge of reference mark as position of maxima or minima of differential 8 Compute mean y coordinate 9 Use computed mean x,y coordinate as center of reference mark Method two—in use:

Step Description

1 Use mouse to point to inside of reference mark

2 Use mouse to point to outside of reference mark

3 Use pointed to inside pixel as starting point

4 Use a threshold pixel level based upon the pointed to inside and outside pixel levels 5 Scan along the x axis until the first pixel equal to or less than the threshold level is found 6 Use the x coordinate of the found pixel as the right and left edge x coordinate 7 Compute the mean x coordinate 8 Scan along the y axis until the first pixel equal to or less than the threshold level is found 9 Use the y coordinate of the found pixel as the top and bottom edge y coordinate 10 Compute the mean y coordinate 11 Use computed mean x,y coordinate as the center of reference mark Improvements being tested:

Method Two Improvement:

Instead of using the coordinate of the pixel equal to or less than the threshold level, use the interpolated factional coordinate:

Left Coordinate=$x$ coordinate+((pixel $x$+1 level)−threshold)/((pixel $x$+1 level)−(pixel $x$ level))

Right Coordinate=x coordinate−((pixel x level)−threshold)/((pixel x level)−(pixel x−1 level))

Top Coordinate=y coordinate+((pixel y+1 level)−threshold)/((pixel y+1 level−(pixel y level))

Bottom Coordinate=y coordinate−((pixel y level)−threshold)/ ((pixel y level −(pixel y−1 level))

This improvement changes method two resolution to much better than its one half pixel.

Improved Estimation of Center of Reference Mark:

Using either method one or two locate the approximate center of the reference mark. Use the first found value of the center as the starting point of a second approximation of the center.

This improvement changes the reproducibility of the found center to better tenth of a pixel.

Positioning by Method of Successive Approximation:
Step Description
1 Use one of the previously disclosed methods of finding the centers
2 Compute the angle error and center of rotation of the image
3 Adjust the image to an approximate standard position and rotation
4 Find the new centers of the reference marks using the same find method
5 Compute the new angle error and center of rotation
6 If the new angle error and center of rotation are too large go to step 3

This improvement changes the reproducibility of the rotation and position of the image to better than five hundredths of a degree and one pixel.

This method can be performed using the current software. However, it requires repeated operator interaction and a substantial amount of time for the repeated adjustment to standard position and rotation.

Step Description
1 Find the centers of the reference marks by either improved method
2 Use the right, left, top, and bottom coordinates to determine the size of the reference mark
3 Use the same method used in the measure image feature to create the pixel pattern across the reference marks as follows:
   a: The diameter plus a small amount through the center parallel to the line between centers
   b: The diameter plus a small amount through the center perpendicular to the line between centers
4 Determine the maximum and minimum pixel level in the pixel patterns
5 Compute the edge coordinates of the half way level in each pattern
6 Use the mean coordinates as the center coordinates for step 3 until the difference between the new center and the previously found center is less than a to be specified fraction of a pixel
7 Use the final found centers as a basis for adjusting the digital image to standard position and rotation This method has the advantage of requiring only one sequence of operator actions and only one adjustment to standard position and rotation.

Review of the Measure Image Pixel Pattern:
Step Description
1 Determine two different position coordinates on the image
2 Compute the equation of the line between the two coordinates
3 Compute the image coordinates of one pixel increments along that line
4 Determine the pixel value at each pixel pattern coordinate
   a: The pixel pattern coordinates may be fractional coordinates
   b: The image pixels are at integral coordinates
   c: The pixel value will be determined by the same method used by the rotate-translate routine—an opposing area weighted mean of the nearest four pixel values Appendix D—Axial Misalignment Calibration for Non-film X-ray Device Images The digitized tomography process requires very precise image registration for it to produce high quality computed images. The requirement is such that every pixel in every source image must be known to the process to within a fraction of a pixel. A method has been developed that provides for such high resolution image registration of film x-ray images. It consisted of a fixture, a setup process, and calibration procedure that assured a very specific geometry of exposure and allowed each digitized film image to be transformed into a standard registration and format. It was specifically because the x-ray source was position immediately overhead the center of rotation of the fixture and the fixture was tilted to the desired angle that axial misalignment of the x-ray images was not encountered.

The current digitized tomography calculations assume the path between the center of the x-ray source and the center of rotation of the non-film fixture's turntable 28 falls on a plane that is perpendicular to the non-film image plate's surface, parallel to the long axis (the "Y" axis) of the non-film image plate, and passes through the center of rotation of the fixture's turntable 28. Since the current fixture is placed horizontally and the x-ray source is moved to the side and angled toward the center of rotation, an axial misalignment is possible without using special alignment procedures and tools. Even a small misalignment can cause serious degradation of the resultant computed digitized tomography views.

Currently, the center of rotation is calibrated using an image of a circular marker placed at the center of rotation in a manner identical to the method used to identify the center of rotation of film images. Because all images can be taken with an identical registration, the three reference mark technique used with film images is not required. However, a second reference mark must be used to measure the axial misalignment of the x-ray optical axis. That marker may be of the same size and material as the center reverence mark but must be displace above the center of rotation by some distance. Since the center position of the marker can be determined to approximately ½ of a pixel width, that distance need only be approximately ½ the maximum possible image radius. The current image plate is 2304 pixels wide with a 200 pixel "gutter" along one edge. That makes the effective radius (2304−200)/2=1145 pixels at 0.005 inches per pixel, that would be 5.724 inches. One half of that would be 2.86 inches.

Using the center coordinates of the two reference markers, the axial misalignment angle can be determined and a correction to the digitized tomography calculations can be applied to the "X" and "Y" axis displacement values. The process is as follows:

Let $x1,y1$ be the pixel coordinate of the center of the center reference mark image. Let $x2,y2$ be the pixel coordinate of the center of the elevated center reference mark image. Let the x-ray optical axis be more or less parallel to the "Y" axis in the positive direction. The distance between centers of the reference marks can be computed by taking the square root of the sum of the squares of the differences between the first and second coordinates: distance=sqrt((x1−x2)*(x1−x2)+(y1−y2)"(y1−y2)). That distance can be divided into the differences between the coordinates to compute the sine and cosine of the misalignment angle: sine of misalignment angle=(x2−x1)/distance and cosine of misalignment angle=(y2−y1)/distance.

The displacement is the normally calculated displacement value and is computed as a function of the image level. The "X" axis displacement value can be computed as the displacement times the sine of the misalignment angle and the "Y" axis displacement value can be computed as the displacement times the cosine of the misalignment angle.

The adjusted displacements are applied to their respective axis calculations as described elsewhere.

Appendix E—Solving General Triangles

Figure 12:
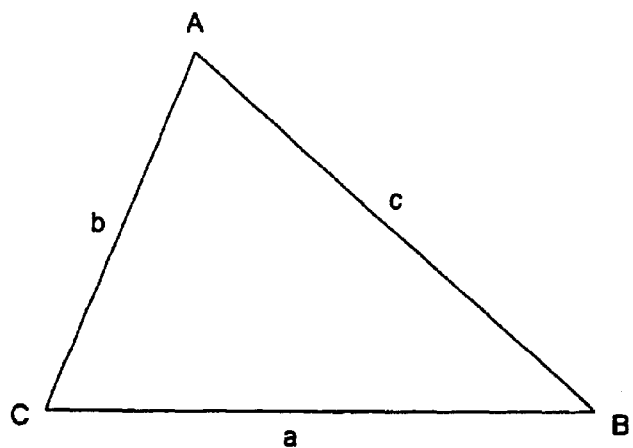
FIG. 12 is a general triangle.

Considering the triangle shown in FIG. 12:

Law of Sines:

$$a \div Sin(A) = b \div Sin(B) = c \div Sin(C)$$

Law of Cosines:

$$c^2 = a^2 + b^2 - 2 \times a \times b \times Cos(C)$$

$$b^2 = a^2 + c^2 - 2 \times a \times c \times Cos(B)$$

$$a^2 = b^2 + c^2 - 2 \times b \times c \times Cos(A)$$

Appendix F—Basic 3D Math

This article is part of *The Win95 Game Programmer's Encyclopedia*

Basic 3D Math

Introduction

The Win95GPE article on basic 2D math lays a lot of the ground work for understanding the information in this article. This section contains some of the basic high-school math needed to understand the equations and graphics primitives used in 3D computer graphics. 3D math is often just a simple extension of the same techniques used for 2D math. An aid to understanding 3D math is to think of it as simply another programming language.

Definition of a 3D Point

Figure 13:
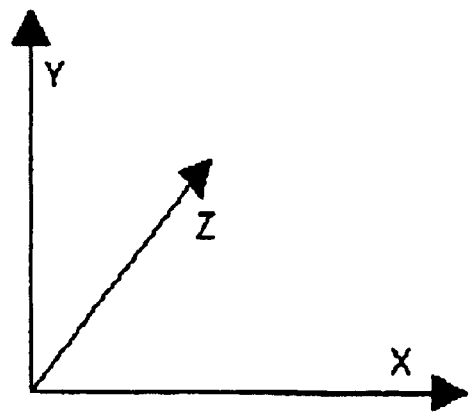
FIG. 13 shows the representation of 3D space in a "left-handed" coordinate system, used in 3D mathematics.

A point is similar to it's 2D counterpart, we simply add an extra component, Z, for the 3rd axis, as shown in FIG. 13. Points are now represented with 3 numbers: <x,y,z>. This particular method of representing 3D space is the "left-handed" coordinate system, which I use throughout this entire article. In the left-handed system the x axis increases going to the right, the y axis increases going up, and the z axis increases going into the page/screen. The right-handed system is the same but with the z-axis pointing in the opposite direction.

Distance Between Two 3D Points

The distance between two points <Ax,Ay,Az> and <Bx,By,Bz> can be found by again using the pythagorus theorem:

$$dx = Ax - Bx$$

$$dy = Ay - By$$

$$dz = Az - Bz$$

$$distance = sqrt(dx*dx + dy*dy + dz*dz)$$

Definition of a 3D Vector

Like it's 2D counterpart, a vector can be thought of in two ways: either a point at <x,y,z> or a line going from the origin <0,0,0> to the point <x,y,z>.

3D Vector addition and subtraction is virtually identical to the 2D case. You can add a 3D vector <vx,vy,vz> to a 3D point <x,y,z> to get the new point <x',y',z'> like so:

$$x' = x + vx$$

$$y' = y + vy$$

$$z' = z + vz$$

Vectors themselves can be added by adding each of their components, or they can be multiplied (scaled) by multiplying each component by some constant k (where k<>0). Scaling a vector by 2 (say) will still cause the vector to point in the same direction, but it will now be twice as long. Of course you can also divide the vector by k (where k<>0) to get a similar result.

To calculate the length of a vector we simply calculate the distance between the origin and the point at <x,y,z>:

$$length = |<x, y, z> - <0, 0, 0>|$$

$$= sqrt((x-0)*(x-0) + (y-0)*(y-0) + (z-0)*(z-0))$$

$$= sqrt(x*x + y*y + z*z)$$

Often in 3D computer graphics you need to convert a vector to a unit vector, i.e., a vector that points in the same direction but has a length of 1. This is done by simply dividing each component by the length:

Let <x,y,z> be our vector, length=sqrt(x*x+y*y+z*z)

$$\text{Unit vector} = \frac{<x, y, z>}{length} = \left| \frac{x}{length}, \frac{y}{length}, \frac{z}{length} \right|$$

(where length=|<x,y,z>|)

Note that if the vector is already a unit vector then the length will be 1, and the new values will be the same as the old.

Definition of a Line

As in 2D, we can represent a line by it's endpoints (P1 and P2) or by the parametric equation:

$$P = P1 + k*(P2 - P1)$$

where k is some scalar value between 0 and 1.

The Dot Product

The dot product between two vectors <Ax,Ay,Az> and <Bx,By,Bz> is calculated like so:

$$A*B = Ax*Bx + Ay*By + Az*Bz$$

If A and B are unit vectors then the dot product is the cosine of the angle between them, so the angle itself can be calculated by taking the inverse cosine of the dot product:

$$theta = invcos(A*B)$$

Fortunately you'll often only need the cosine of the angle between 2 vectors and not the angle itself, so the expensive step of calculating the inverse cosine can be skipped.

Definition of a Plane

Figure 14:
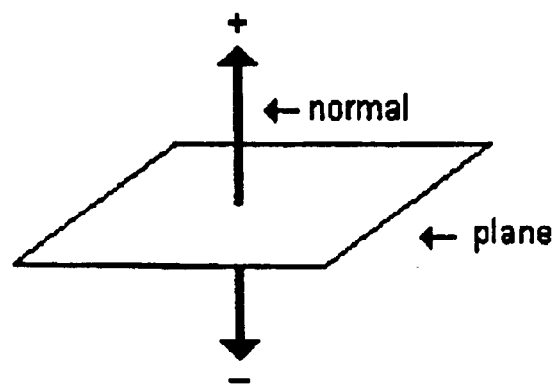
FIG. 14 illustrates a plane showing normal as the direction that the surface of the plane is facing, used in 3D mathematics.

A plane is an infinitely wide flat polygon-type surface. A plane can be defined by a normal <nx,ny,nz> and a scalar value k. The normal can be thought of as representing the direction that the surface of the plane is facing, i.e., it's a directional vector at a right angle to the plane, as shown in FIG. 14. We can imagine the normal as describing an infinitely long line stretching off to infinity in either direction, and that a plane can slide up and down along this line. In the plane equation the value k specifies where exactly on this line the plane sits.

The equation for the plane uses the dot product:

$$<x,y,z>*<nx,ny,nz>=k$$

All points <x,y,z> that actually lie on the plane itself will satisfy this equation. This gives us a convenient method for determining which side of a plane any given point <x,y,z> is:

$$<x,y,z>*<nx,ny,nz>=k \text{ Point is in plane}$$

$$<x,y,z>*<nx,ny,nz>>k \text{ Point is on one side of plane}$$

$$<x,y,z>*<nx,ny,nz><k \text{ Point is on other side of plane}$$

The vector <nx,ny,nz> and scalar k are unique to every plane (a way of calculating them is shown below). These equations are helpful in performing back-face culling. Substitute the view point into the equation, if the value comes out less than k then you know that you are facing the "back" side of the polygon and thus don't need to draw it.

The Cross Product

If you have 2 vectors then the cross product will return a vector which is perpendicular (i.e., at a right angle) to both of them. The cross product between two vectors <Ax,Ay,Az> and <Bx,By,Bz> is:

$$A \times B = <Ay*Bz-Az*By, Az*Bx-Ax*Bz, Ax*By-Ay*Bx>$$

Note that while the dot product returns a single scalar value, the cross product returns a vector.

Taking the cross-product between the x axis <1,0,0> and y axis <0,1,0> gives us:

$$<1,0,0> \times <0,1,0> = <0*0-0*1, 0*1-1*0, 1*1-0*0>$$
$$= <0,0,1>$$

which is of course the z axis and is indeed perpendicular to both vectors.

Calculating a Plane from 3 Points

Figure 15:
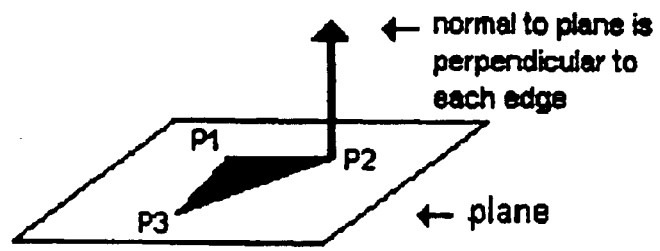
FIG. 15 illustrates the calculation of a plane from 3 given points, used in 3D mathematics.
Figure 16:
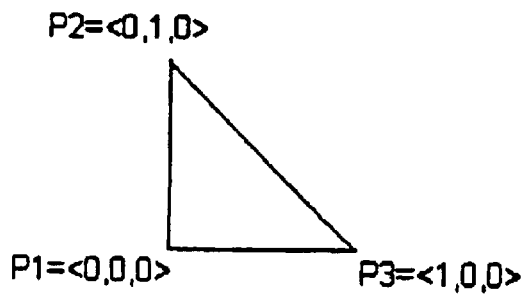
FIG. 16 illustrates 3 points stored in a clockwise direction in the x/y plane, used in 3D mathematics.

To calculate a plane from 3 given points we first calculate the normal. If we imagine the 3 points form three edges in the plane then we can take two of the edges and calculate the cross-product between them. The resulting directional vector will be the normal, and then we can plug any of the 3 known points into the plane equation to solve for k. For points p1,p2 and p3 we get:

$$normal=(p1-p2) \times (p3-p2)$$

$$k=normal*p1$$

as shown in FIG. 15. Note that it is extremely important to keep track of which direction your points are stored in. Take 3 points stored in clockwise direction in the x/y plane, as shown in FIG. 16. The normal to the plane these 3 points define is:

$$normal = (p1-p2) \times (p3-p2)$$
$$= (0,-1,0) \times (1,-1,0)$$
$$= <(-1)*0-0*(-1), 0*1-0*0, 0*(-1)-(-1)*1>$$
$$= <0,0,1>$$

i.e., the z axis. If we were to store the points counter-clockwise the normal calculated would be <0,0,−1>, which is still the z axis but in the "opposite" direction. It's important to keep track of these things since we often need plane equations to be correct in order to determine which side of a polygon an object (such as the view point) is on.

3D Rotation

In the Win95GPE article on basic 2D math we saw how a 2D point <x,y> be rotated around the origin <0,0>. In 3D this is the same as rotating the point around the z axis (the z value remains the same). We can slightly modify this basic equation to get rotation around all three axis:

Rotation about the x axis:

$$x'=x$$

$$y'=(\cos é*y)-(\sin é*z)$$

$$z'=(\sin é*y)+(\cos é*z)$$

Rotation about the y axis:

$$x'=(\cos é*x)+(\sin é*z)$$

$$y'=y$$

$$z'=-(\sin é*x)+(\cos é*z)$$

Rotation about the z axis:

$$x'=(\cos é*x)-(\sin é*y)$$

$$y'=(\sin é*x)+(\cos é*y)$$

$$z'=z$$

Rotating a point around an arbitrary axis is a tad complex, so I'll discuss how to do this in the article on matrices (since they're an ideal tool for performing these types of rotations). It's fairly easy to expand the steps in that article for "regular" 3D math.

Intersections

This section shows how to calculate intersections between various objects. This is particularly handy for things like collision detection.

Intersection Between a Line and a Plane

This occurs at the point which satisfies both the line and the plane equations.

$$\text{Line equation: } p=org+u*dir \quad (1)$$

$$\text{Plane equation: } p*normal-k=0. \quad (2)$$

Substituting (1) into (2) and rearranging we get:

$$(org+u*dir)*normal-k=0$$

i.e., $u*dir*normal=k-org*normal$ i.e., $u=(k-org*normal)/(dir*normal)$

If (d*normal)=0 then the line runs parallel to the plane and no intersection occurs. The exact point at which intersection does occur can be found by plugging u back into the line equation in (1).

Intersection Between a Line and a Sphere

This occurs at the point which satisfies both the line and the sphere equations.

Line equation: $p=org+u*dir$    (1)

Sphere equation: $|p-origin|=radius$    (2)

Substituting (1) into (2) we get:

$|(org+u*dir)-origin|=radius$ i.e., $(org+u*dir-origin)^2=radius^2$

Which can be rearranged into the following form:

$u^2*dir^2+u*2*dir*(org-origin)+(org-origin)^2$

This is a quadratic equation in u which can thus be solved with the following formula:

$u=-B+/-sqrt(B^2-4AC)2A$ where $A=dir^2$ $B=2*dir*(org-origin)$ $C=(org-origin)^2$ Note that $dir^2$ means $dir*dir$, i.e., the dot product of dir with itself. The same applies to org-origin in C. dir *(org-origin) in B is also a dot product.

To get the actual points of intersection you plug the 2 resulting u values into the line equation.

If A=0 then the line does not intersect the sphere. If $sqrt(B^2-4AC)=0$ then the line is tangent to the surface of the sphere and there is only one point of intersection at $u=-B/2A$.

Intersection Between Three Planes

In order to find the point <x,y,z> of intersection between three planes ($p*n1-k1=0$, $p*n2-k2=0$ and $p*n3-k3=0$) we can use matrices (Appendix G; in particular read the section on solving simultaneous equations). If we place all three equations into a matrix then we can see that the following rule will apply:

$$\begin{vmatrix} n1 \cdot x & n1 \cdot y & n1 \cdot z & -k1 \\ n2 \cdot x & n2 \cdot y & n2 \cdot z & -k2 \\ n3 \cdot x & n3 \cdot y & n3 \cdot z & -k3 \\ 0 & 0 & 0 & 1 \end{vmatrix} \times \begin{vmatrix} x \\ y \\ z \\ 1 \end{vmatrix} = \begin{vmatrix} 0 \\ 0 \\ 0 \\ 1 \end{vmatrix}$$

By rearranging this equation we can solve for <x,y,z>:

$$\begin{vmatrix} x \\ y \\ z \\ 1 \end{vmatrix} = \begin{vmatrix} n1 \cdot x & n1 \cdot y & n1 \cdot z & -k1 \\ n2 \cdot x & n2 \cdot y & n2 \cdot z & -k2 \\ n3 \cdot x & n3 \cdot y & n3 \cdot z & -k3 \\ 0 & 0 & 0 & 1 \end{vmatrix}^{-1} \times \begin{vmatrix} 0 \\ 0 \\ 0 \\ 1 \end{vmatrix}$$

Thus if we calculate the inverse of the matrix then the 4th column will contain the point of intersection. (If the matrix has no inverse then at least two of the planes are parallel and there is no point of intersection).

Note that because of the constant terms we could instead use a 3×3 matrix for a more optimized solution:

$$\begin{vmatrix} x \\ y \\ z \end{vmatrix} = \begin{vmatrix} n1 \cdot x & n1 \cdot y & n1 \cdot z \\ n2 \cdot x & n2 \cdot y & n2 \cdot z \\ n3 \cdot x & n3 \cdot y & n3 \cdot z \end{vmatrix} \times \begin{vmatrix} k1 \\ k2 \\ k3 \end{vmatrix}$$

Intersection Between Two Planes

The line ($p=org+u*dir$) of intersection between two planes ($p*n1-k1=0$ and $p*n2-k2=0$) is perpendicular to each plane's normal, i.e.:

$dir=n1 \times n2$

What we can now do is assume there is a third plane perpendicular to both planes, i.e., one which has a normal of dir. All that remains is to find the k value for this plane and then find the point of intersection between all three planes, as shown in the previous section. For simplicity we can assume this third k value to be 0 and use the resulting point as our org value:

$$\begin{vmatrix} org \cdot x \\ org \cdot y \\ org \cdot z \\ 1 \end{vmatrix} = \begin{vmatrix} n1 \cdot x & n1 \cdot y & n1 \cdot z & 0 \\ n2 \cdot x & n2 \cdot y & n2 \cdot z & 0 \\ dir \cdot x & dir \cdot y & dir \cdot z & 0 \\ 0 & 0 & 0 & 1 \end{vmatrix} \times \begin{vmatrix} k1 \\ k2 \\ 0 \\ 1 \end{vmatrix}$$

Copyright (c) 1997 Mark Feldman (pcgpe@geocities.com)—All Rights Reserved This article is part of *The Win95 Game Programmer's Encyclopedia* Please retain this footer if you distribute this file.

Appendix G—Matrices

This article is part of *The Win95 Game Programmer's Encyclopedia*

Matrices

Introduction

Matrices are extremely handy for writing fast 3D programs. They are just a 4×4 list of numbers, but they do have 2 very important properties:

1) They can be used to efficiently keep track of transformations, i.e., actions which occur in a VR program such as movement, rotation, zoom in/out etc.

2) A single matrix can represent an infinite number of these transformations in any combination. Let's say the user in your program walks forward, turns left, looks up, backs up a bit etc . . . All you need to do is keep a copy of a master matrix in memory and adjust it as the user does these things. At any point you then use this one matrix to figure out where everything in your virtual world should be drawn on the screen.

A transformation is simply a way of taking a set of points and modifying them in some way to get a new set of points. For example, if the user moves 10 units forward in a certain direction then the net result is the same as if all objects in the world moved 10 units in the opposite direction.

In 3D computer graphics it is often convenient to assume that the view-point is always at the origin <0,0,0>. Not only does it make it easier to render a scene but it often makes it a lot faster as well. Instead of having the user move around the world we can keep the user at the origin and make the objects move around instead. From the users point of view it will look exactly the same. Matrices are a fast and convenient tool to perform these transformations.

A Point in Space

As mentioned above, a point or vector can be represented in 3D space as <x,y,z>. When using matrix math it helps to represent it as <x,y,z,w>. That extra w there helps make things like movement easier to deal with. If we have a point in 3D space we can convert it to this new format by setting w to 1. In this text I'll be representing all points in space as a column vector:

$$\begin{vmatrix} x \\ y \\ z \\ w \end{vmatrix} < -w = 1$$

Modifying the Position of a Point

Let's say we want to take any point <x,y,z,w> given and do something to it to get a new point. A row vector can be used to represent how we want to change a point:

These values contain the info on how we want to change the point → $|A \ B \ C \ D| \cdot \begin{vmatrix} x \\ y \\ z \\ w \end{vmatrix}$ ← This is our point in 3D space To figure out how the row vector |A B C D| changes a point, we can visualize lying the point's column vector on it's side on top of it like this:

$$\begin{vmatrix} x & y & z & w \\ A & B & C & D \end{vmatrix} = (x*A)+(y*B)+(z*C)+(w*D)$$

Compare this to the article on basic 3D math (Appendix F) and you'll see that we are in fact taking the dot product of the two vectors. What we do above is multiply each top item by the item under it and add the results up to get the answer.

Let's say we want to be able to take any point <x,y,z,w> and figure out the coordinates for the point <x',y',z',1> which is exactly 4 units to the "right" of it, i.e., the point which is 4 units further along the axis. We can do this by using 4 row vectors. The first one will calculate the new x point (x'), the next one the new y point (y') and so on. First let's look at calculating x'.

We know that the new x point can be calculated like this: x'=x+4, so a row vector to calculate this would be:

|1 0 0 4| i.e. when we multiply this out by a point <x,y,z,w> we'll get:

(x*1)+(y*0)+(z*0)+(w*4)=x+4

We also know that y'=y, z'=z and w=1, so we can calculate the row vectors for each of the other values, and stack them all on top of each other:

x row vector → $\begin{vmatrix} 1 & 0 & 0 & 4 \\ 0 & 1 & 0 & 0 \\ 0 & 0 & 1 & 0 \\ 0 & 0 & 0 & 1 \end{vmatrix}$ 
$x' = 1*x+0*y+0*z+4 = x+4$
$x' = 0*x+1*y+0*z+0 = y$
$x' = 0*x+0*y+1*z+0 = z$
$x' = 0*x+0*y+0*z+1 = 1$ y row vector →
z row vector →
1 row vector →

And VOILA! That's what a matrix is! To take a point <x,y,z,w> and calculate the new point we just multiply the point by each of the row vectors.

Here's a more generic representation of what we are doing:

$$\begin{vmatrix} x' \\ y' \\ z' \\ w' \end{vmatrix} = \begin{vmatrix} M11 & M12 & M13 & M14 \\ M21 & M22 & M23 & M24 \\ M31 & M32 & M33 & M34 \\ M41 & M42 & M43 & M44 \end{vmatrix} \begin{vmatrix} x \\ y \\ z \\ w \end{vmatrix}$$

In this case <x,y,z,w> is the point we are popping in, <x',y',z',w'> is the point we'll be getting out, and each number in the matrix is represented by Mij, where i=row number and j=column number.

Following the line of reasoning above, we can figure out how to calculate the new point based on the given point and the matrix:

$x'=(x*M11)+(y*M12)+(z*M13)+M14$ $y'=(x*M21)+(y*M22)+(z*M23)+M24$ $z'=(x*M31)+(y*M32)+(z*M33)+M34$ $w'=(x*M41)+(y*M42)+(z*M43)+M44$

In practice, we don't really need that last equation, we know that it will always equal 1 so we don't have to calculate it.

Plugging a point into a matrix like this and getting a new point out is called "transforming" a point by a matrix, just keep that in mind so you know what to call your procedure to do it!

A few of the more commonly used matrices follow.

Doing Nothing

You often need a matrix to pop out exactly the same point as was plugged in. The matrix to do this is called the identity matrix:

$$\begin{vmatrix} 1 & 0 & 0 & 0 \\ 0 & 1 & 0 & 0 \\ 0 & 0 & 1 & 0 \\ 0 & 0 & 0 & 1 \end{vmatrix} \begin{matrix} x' = x \\ y' = y \\ z' = z \end{matrix}$$

Translation

A translation is simply adding (or subtracting) a point to any given point. Let's say you want to add TX to x, TY to y and TZ to z. The matrix to do this is:

$$\begin{vmatrix} 1 & 0 & 0 & tx \\ 0 & 1 & 0 & ty \\ 0 & 0 & 1 & tz \\ 0 & 0 & 0 & 1 \end{vmatrix} \begin{matrix} x' = x+tx \\ y' = y+ty \\ z' = z+tz \end{matrix}$$

Scaling

Sometimes we may need to scale a point, i.e., multiply each axis by a given number. This is handy for things like zoom effects.

$$\begin{vmatrix} sx & 0 & 0 & 0 \\ 0 & sy & 0 & 0 \\ 0 & 0 & sz & 0 \\ 0 & 0 & 0 & 1 \end{vmatrix} \begin{matrix} x' = sx*x \\ y' = sy*y \\ z' = sz*tz \end{matrix}$$

Of course, if you only want to scale along the X axis (say) then you simply set SX to the scale value and set SY and SZ to 1.

Basic Rotations

We can rotate things around the x axis, the y axis, or the z axis. Each axis forms a line in 3D space. We can also rotate things around any arbitrary line. This is handy if we want to do effects like objects rotating about their own axis (which will be discussed later).

The matrix for rotating around the x axis by angle é is:

$$\begin{vmatrix} 1 & 0 & 0 & 0 \\ 0 & \cos é & -\sin é & 0 \\ 0 & \sin é & \cos é & 0 \\ 0 & 0 & 0 & 1 \end{vmatrix} \begin{aligned} x' &= x \\ y' &= (\cos é)*y - (\sin é)*z \\ z' &= (\sin é)*y + (\cos é)*z \end{aligned}$$

The matrix for rotating around the y axis by angle é is:

$$\begin{vmatrix} \cos é & 0 & \sin é & 0 \\ 0 & 1 & 0 & 0 \\ -\sin é & 0 & \cos é & 0 \\ 0 & 0 & 0 & 1 \end{vmatrix} \begin{aligned} x' &= (\cos é)*x + (\sin é)*z \\ y' &= y \\ z' &= -(\sin é)*x + (\cos é)*z \end{aligned}$$

And the matrix for rotating around the z axis by angle é is:

$$\begin{vmatrix} \cos é & -\sin é & 0 & 0 \\ \sin é & \cos é & 0 & 0 \\ 0 & 0 & 1 & 0 \\ 0 & 0 & 0 & 1 \end{vmatrix} \begin{aligned} x' &= (\cos é)*x - (\sin é)*y \\ y' &= (\sin é)*x + (\cos é)*y \\ z' &= z \end{aligned}$$

Mirroring

Figure 17:
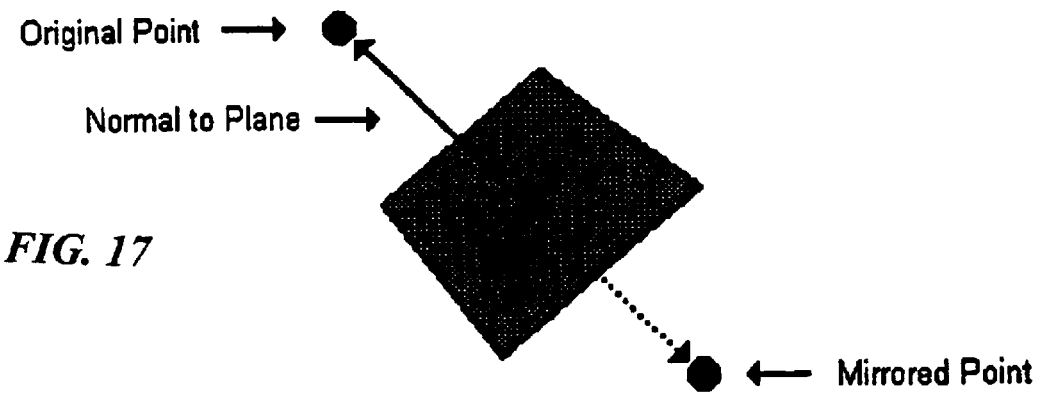
FIG. 17 illustrates mirroring wherein all points are flipped about an arbitrary plane in 3D space, used in matrix mathematics.

Mirroring involves flipping all points about an arbitrary plane in 3D space, as illustrated in FIG. 17. From the diagram in FIG. 17 we can easily see that to mirror a point we need to:

1) Calculate the distance of the point from the plane
2) Move the point in the opposite direction to the plane normal a distance of 2* dist.

The distance of a point from a plane can be calculated easily with the plane equation:

$$dist = p * normal + k$$

(Normally this equation assumes that the plane normal is a unit vector. In this particular case however this is not a requirement).

Based on the information above we can see that the final mirror equation is:

$$\begin{aligned} p' &= p - 2*dist*normal \\ &= p - 2*(p*normal + k)*normal \\ &\phantom{=} p - 2*(p \cdot x*normal \cdot x + p \cdot y*normal \cdot \\ &\phantom{=} y + p \cdot z*normal \cdot z + k)*normal \end{aligned}$$

Expanding this out we get the equation for each element in p':

$$p'.x = p.x - 2*p.x*nx*nx + 2p.y*ny*nx + 2*p.z*nz*nx + 2*k*nx$$

$$p'.y = p.y - 2*p.x*nx*ny + 2p.y*ny*ny + 2*p.z*nz*ny + 2*k*ny$$

$$p'.z = p.z - 2*p.x*nx*nz + 2p.y*ny*nz + 2*p.z*nz*nz + 2*k*nz$$

where $<nx,ny,nz>$ = normal. Thus the final mirror matrix for any given plane $p*<nx,ny,nz>+k=0$ is:

$$\begin{vmatrix} 1-2*nx*nx & -2*nx*ny & -2*nx*nz & -2*nx*k \\ -2*ny*nx & 1-2*ny*ny & -2*ny*nz & -2*ny*k \\ -2*nz*nx & -2*nz*ny & 1-2*nz*nz & -2*nz*k \\ 0 & 0 & 0 & 1 \end{vmatrix}$$

(Note the common terms: m[0][1]=m[1][0], m[0][2]=m[2][0], and m[1][2]=m[2][1]).

Multiplying Matrices

So now that we know how to represent each of the different types of matrix operations, how do we combine them? By multiplying two matrices together:

$$P = B \times A$$

If transforming a point by A gives one effect, and transforming it by B gives another, then transforming it by P alone gives you the same result as if you had transformed it by A then by B. You can keep multiplying a matrix by as many other matrices as you like, and each time the end product will contain the info for all of them in the correct order.

To multiply B by A, you treat each column in A as a separate column vector, and transform it by matrix B to get the new column. Let's look at doing it for the first column in A:

$$\begin{vmatrix} P11 \\ P21 \\ P31 \\ P41 \end{vmatrix} = \begin{vmatrix} B11 & B12 & B13 & B14 \\ B21 & B22 & B23 & B24 \\ B31 & B32 & B33 & B34 \\ B41 & B42 & B43 & B44 \end{vmatrix} \begin{vmatrix} A11 \\ A21 \\ A31 \\ A41 \end{vmatrix}$$

So that first column of P will be:

$$\begin{vmatrix} (A11*B11) + (A21*B12) + (A31*B13) + (A41*B14) \\ (A11*B21) + (A21*B22) + (A31*B23) + (A41*B24) \\ (A11*B31) + (A21*B32) + (A31*B33) + (A41*B34) \\ (A11*B41) + (A21*B42) + (A31*B43) + (A41*B44) \end{vmatrix}$$

We need to split the A matrix up into it's 4 column vectors and transform each column vector by matrix B to get 4 new column vectors:

$$\begin{vmatrix} P11 \\ P21 \\ P31 \\ P41 \\ P12 \\ P22 \\ P32 \\ P42 \\ P13 \\ P23 \\ P33 \\ P43 \\ P14 \\ P24 \\ P34 \\ P44 \end{vmatrix} = \begin{vmatrix} B11 & B12 & B13 & B14 \\ B21 & B22 & B23 & B24 \\ B31 & B32 & B33 & B34 \\ B41 & B42 & B43 & B44 \\ B11 & B12 & B13 & B14 \\ B21 & B22 & B23 & B24 \\ B31 & B32 & B33 & B34 \\ B41 & B42 & B43 & B44 \\ B11 & B12 & B13 & B14 \\ B21 & B22 & B23 & B24 \\ B31 & B32 & B33 & B34 \\ B41 & B42 & B43 & B44 \\ B11 & B12 & B13 & B14 \\ B21 & B22 & B23 & B24 \\ B31 & B32 & B33 & B34 \\ B41 & B42 & B43 & B44 \end{vmatrix} \begin{vmatrix} A11 \\ A21 \\ A31 \\ A41 \\ A12 \\ A22 \\ A32 \\ A42 \\ A13 \\ A23 \\ A33 \\ A43 \\ A14 \\ A24 \\ A34 \\ A44 \end{vmatrix}$$

The resulting matrix is then made by combing these 4 column vectors back into a single matrix:

$$B \times A = \begin{vmatrix} P11 & P12 & P13 & P14 \\ P21 & P22 & P23 & P24 \\ P31 & P32 & P33 & P34 \\ P41 & P42 & P43 & P44 \end{vmatrix}$$

One thing to keep in mind is that the bottom row in any matrix will always be [0 0 0 1], so we can use this to slightly speed up matrix multiplication. Here's a general algorithm which will multiply 2 matrices:

```
Let A and B be our matrices, P will be the result (B x A).
var i,j : integer;
for i := 0 to 2 do
    for j := 0 to 3 do
        begin
            P [i] [j] := 0;
            for k := 0 to 3 do
                P [i][j] := P [i] [j] + B [i] [k] * A [k][j];
        end;
P [3] [0] := 0; { Set the bottom row to 0 0 0 1 }
P [3] [1] := 0;
P [3] [2] := 0;
P [3] [3] := 1.
```

The Inverse Matrix

Let's say we have two matrices A and B. If the following is true:

$$A \times B = B \times A = \begin{vmatrix} 1 & 0 & 0 & 0 \\ 0 & 1 & 0 & 0 \\ 0 & 0 & 1 & 0 \\ 0 & 0 & 0 & 1 \end{vmatrix}$$

then we say that B is the __inverse__ of A (and visa-versa). If you transform a point P1 by matrix A then you'll get a new point P2. If you then transform P2 by matrix B, it'll return P1. The two matrixes have the same effect but in "opposite" directions, e.g., if A moves all points 5 spaces to the "left" then B will move them 5 spaces to the "right". Similarly if A rotates space around a particular axis one way then B will rotate by the same amount around the same axis in the opposite direction.

There are several methods for calculating the inverse of a matrix, for large matrices the Gaussian method is preferred. Gaussian uses a technique called of "row reduction", first we create a large matrix like so:

| This is the matrix we are trying to find the inverse of | | | | This is the identity matrix | | | |
|---|---|---|---|---|---|---|---|
| A11 | A12 | A13 | A14 | 1 | 0 | 0 | 0 |
| A21 | A22 | A23 | A24 | 0 | 1 | 0 | 0 |
| A31 | A32 | A33 | A34 | 0 | 0 | 1 | 0 |
| A41 | A42 | A43 | A44 | 0 | 0 | 0 | 1 |

Our goal is to perform various "elementary row operations" on this matrix to put it in the following form:

| Identity matrix | | | | The inverse | | | |
|---|---|---|---|---|---|---|---|
| 1 | 0 | 0 | 0 | B11 | B12 | B13 | B14 |
| 0 | 1 | 0 | 0 | B21 | B22 | B23 | B24 |
| 0 | 0 | 1 | 0 | B31 | B32 | B33 | B34 |
| 0 | 0 | 0 | 1 | B41 | B42 | B43 | B44 |

In the above matrices A is our initial matrix and B will be the inverse of A.

There are three kinds of elementary row operations we can use:

RULE 1—Interchange two rows.
RULE 2—Multiply any row by a constant other than 0.
RULE 3—Add a constant multiple of any row to another row.

Here is the basic algorithm to figure out which steps to perform as well as their order (this algorithm assumes that the bottom row of a matrix is always [0 0 0 1]):

```
var i,j,row : integer;
multiple, divisor : real;
    A : array[0..3] [0..7] of real;
Set values A[0..3] [0..3] to our 4x4 matrix
Set values A[0..3] [4..7] to the 4x4 identity matrix
{ Loop through each row }
for row := 0 to 3 do
    begin
        { Make sure this row doesn't have a 0 in A[row] [row]
        (use RULE 1) }
        if A[row] [row] = 0 then
            begin
                find a row i where (i>row) and (i<3) and (A[i] [row]
                <> 0)
                interchange rows 'i' and 'row'
            end;
        { Divide this row by a constant so that A[row] [row] =
        1 (use RULE 2)
}
    divisor := A[row] [row];
    for j := 0 to 7 do
        A[row] [j] := A [row] [j]/divisor;
    { Make all other elements in column 'row' a 0 (use RULE 3) }
    for i := 0 to 2 do
        if i <> row then
            begin
                multiple := A[i] [row];
                for j := 0 to 7 do
                    A [i] [j] := A [i] [j] − multiple * A [row] [j];
            end;
    end;
Return the matrix in the values A [0..3] [4..7]
```

There are cases where a matrix doesn't have an inverse. If this happens then the first part of the algorithm above will fail, you won't be able to find a row where A[i][row] !=0. However, if you stick to the "normal" 3D operations discussed in this article (translation, rotation, scaling etc) then the matrices produced will always have an inverse.

One other very important thing to remember is that due to round-off errors you will often get values in the matrix such as 0.000001 which are supposed to be 0. When looking for a row where A[i][row]!=0 you must keep this in mind, and instead check that the absolute value is larger than some small number (e.g., 0.0001).

Rotating Around an Arbitrary Axis

Let's say we need to rotate space by about an arbitrary axis defined by the line o+kd (where o is the origin point <ox,oy,oz> and d is the directional vector <dx,dy,dz>). Here are the steps needed to perform this rotation:

1) First translate all of space so that the line of rotation starts at the origin. Do this by subtracting the line's origin point from all points. Here is the matrix needed, along with it's inverse:

$$F = \begin{vmatrix} 1 & 0 & 0 & -ox \\ 0 & 1 & 0 & -oy \\ 0 & 0 & 1 & -oz \\ 0 & 0 & 0 & 1 \end{vmatrix} \quad F' = \begin{vmatrix} 1 & 0 & 0 & ox \\ 0 & 1 & 0 & oy \\ 0 & 0 & 1 & oz \\ 0 & 0 & 0 & 1 \end{vmatrix}$$

2) Next rotate space around the z axis until the line of rotation lies in the x/z plane:

$$G = \begin{vmatrix} dx/v & dy/v & 0 & 0 \\ -dy/v & dx/v & 0 & 0 \\ 0 & 0 & 1 & 0 \\ 0 & 0 & 0 & 1 \end{vmatrix} \quad G' = \begin{vmatrix} dx/v & -dy/v & 0 & 0 \\ dy/v & dx/v & 0 & 0 \\ 0 & 0 & 1 & 0 \\ 0 & 0 & 0 & 1 \end{vmatrix}$$

where v=SQRT(dx*dx+dy*dy). You will now have a new line of rotation with one end at the origin and the other end at the point <v,0,dz>.

3) Now rotate space around the y axis until the line of rotation lies along the z axis:

$$H = \begin{vmatrix} dz/w & 0 & -v/w & 0 \\ 0 & 1 & 0 & 0 \\ v/w & 0 & dz/w & 0 \\ 0 & 0 & 0 & 1 \end{vmatrix} \quad H' = \begin{vmatrix} dz/w & 0 & v/w & 0 \\ 0 & 1 & 0 & 0 \\ -v/w & 0 & dz/w & 0 \\ 0 & 0 & 0 & 1 \end{vmatrix}$$

where w=SQRT(v*v+dz*dz)=SQRT(dx*dx+dy*dy+dz*dz).

4) At this point the axis of rotation is a line lying along the z axis between the points <0,0,0> and <0,0,w>, so you can rotate space around the z axis by:

$$W = \begin{vmatrix} \cos A & -\sin A & 0 & 0 \\ \sin A & \cos A & 0 & 0 \\ 0 & 0 & 1 & 0 \\ 0 & 0 & 0 & 1 \end{vmatrix}$$

5) So to do the entire rotation you must first transform space by F,G and H to align the axis of rotation along the z axis, then you do the actual rotation around the z axis using matrix W, then you transform space by H', G' and F' to put everything back into place. By multiplying these matrices together you can create a single matrix to do the entire rotation:

P=F'×G'×H'×W×H×G×F

Any points transformed by this matrix will be rotated about the line by an angle of A.

If the term 1/v in the G and G' matrices result in a singularity, it can be fixed by replacing G and G' with the identity matrix when v is 0.

Solving Simultaneous Equations

Imagine that we have the following equations:

a*x+b*y+c*z+d=0 e*x+f*y+g*z+h=0 i*x+j*y+k*z+l=0

Now imagine that we need to find a point <x,y,z> which satisfies all 4 equations. These equations contain 12 unknowns, so it's clear that it would be very difficult to solve using "regular" algebra.

Matrices on the other hand provide us with a very useful tool for solving such problems. We can create a matrix like this:

$$\begin{vmatrix} 0 \\ 0 \\ 0 \\ 1 \end{vmatrix} = \begin{vmatrix} a & b & c & d \\ e & f & g & h \\ i & j & k & l \\ 0 & 0 & 0 & 1 \end{vmatrix} \begin{vmatrix} x \\ y \\ z \\ 1 \end{vmatrix}$$

When we expand this out (as I showed earlier on in this article) we get the 4 equations we are trying to solve. We also know that we can use the inverse matrix to rearrange the equation:

$$\begin{vmatrix} x \\ y \\ z \\ 1 \end{vmatrix} = \begin{vmatrix} a & b & c & d \\ e & f & g & h \\ i & j & k & l \\ 0 & 0 & 0 & 1 \end{vmatrix}^{-1} \begin{vmatrix} 0 \\ 0 \\ 0 \\ 1 \end{vmatrix}$$

These equations will expand out to the following:

x=A*0+B*0+C*0+D*1=D y=E*0+F*0+G*0+H*1=H z=I*0+J*0+K*0+L*1=L (The letters have been capitalized since the inverse matrix will typically contain different values than the original).

In summary, if we create a matrix from 3 parametric equations and then calculate the inverse of that matrix then the 4th column will contain a point which satisfies all 3 equations. If the inverse matrix operation fails then we know that the problem has no solution (or an infinite number of solutions).

Incidentally the fact that we'll only wind up using the 4th column can help in optimizing this procedure since we don't need to calculate the entire matrix.

2D Matrices

In this text I've been using 4×4 matrices for 3D coordinate geometry, but it's just as easy to use a smaller matrix for 2D (or higher), we simply drop the z term.

2D matrices are of the form:

$$\begin{vmatrix} x' \\ y' \\ 1 \end{vmatrix} = \begin{vmatrix} M11 & M12 & M13 \\ M21 & M22 & M23 \\ 0 & 0 & 1 \end{vmatrix} \begin{vmatrix} x \\ y \\ 1 \end{vmatrix}$$

i.e., x'=M11*x+M12*y+M13 y=M21*x+M22*y+M23

The 2D identity matrix is:

$$\begin{vmatrix} 1 & 0 & 0 \\ 0 & 1 & 0 \\ 0 & 0 & 1 \end{vmatrix} \begin{matrix} x' = x \\ y' = y \end{matrix}$$

To translate by <tx, ty>:

$$\begin{vmatrix} 1 & 0 & tx \\ 0 & 1 & ty \\ 0 & 0 & 1 \end{vmatrix} \begin{matrix} x' = x + tx \\ y' = y + ty \end{matrix}$$

To scale by <sx, sy>:

$$\begin{vmatrix} sx & 0 & 0 \\ 0 & sy & 0 \\ 0 & 0 & 1 \end{vmatrix} \begin{matrix} x' = x*sx \\ y' = y*sy \end{matrix}$$

And to rotate about the origin by A radians:

$$\begin{vmatrix} \cos(A) & -\sin(A) & 0 \\ \sin(A) & \cos(A) & 0 \\ 0 & 0 & 1 \end{vmatrix} \begin{matrix} x' = \cos(A)*x - \sin(A)*y \\ y' = \sin(A)*x + \cos(A)*y \end{matrix}$$

Copyright (c) 1997 Mark Feldman (pcgpe@geocities.com)—All Rights Reserved This article is part of *The Win95 Game Programmer's Encyclopedia* Please retain this footer if you distribute this file.

What is claimed is:

1. In a digitized tomosynthesis method for obtaining 3D volumetric imaging of an object in which a ray of energy from a source travels through the object to impinge on an energy sensor having a determined pixel size defining an image plane and in which the object is rotated about an axis that intersects the energy sensor whereby an image is acquired by the energy sensor at successive rotational positions of the object, the improvement according to which a coordinate of the source position with respect to the sensor is determined, comprising the steps of:

placing a first registration marker that is substantially opaque to the energy on a first location proximate the energy sensor and along the object's axis of rotation;

obtaining a first shadow image corresponding to the first registration marker by exposing the first registration marker to energy from the energy source;

placing a second registration marker that is substantially opaque to the energy on a calibration post disposing the second registration marker at a location distal from the energy sensor spaced at a predetermined distance from said first location along the object's axis of rotation;

obtaining a second shadow image of the calibration post corresponding to the second registration marker by exposing the second registration marker to energy from the energy source;

determining the distance from the source to the energy sensor at the intersection of the axis with the energy sensor;

determining the height of the second marker;

determining the central coordinates of the first and second marker shadows;

computing the azimuth;

computing the elevation angle; and using the elevation angle and azimuth to compute the coordinate of the source position with respect to the sensor.

2. The method of claim 1 in which the azimuth is computed from a triangle formed by the marker centers and image axes.

3. The method of claim 1 in which the elevation angle is computed by:

computing an angle A as the arc tangent of (the height of the calibration post divided by the length of the shadow of the calibration post);

computing an angle B as the arc sine of (the sine of angle A times the shadow of the calibration post divided by the source distance);

computing an angle C as 180°−A−B;

computing a distance c as the square root of $Hp^2$ plus $Ls^2-2.0 \times Hp \times Ls \times$ cosine (C), where Hp is the height of the calibration post and Ls is the length of the shadow of the calibration post;

computing the height y of the source above the image plane as c×sine (A); and computing the elevation angle as arc sine of (y divided by the source distance).

4. The method of claim 1 in which the energy is in the form of electromagnetic radiation.

5. The method of claim 4 in which the electromagnetic radiation is x-ray radiation.

6. The method of claim 1 in which the energy sensor is an image plate.

7. The method of claim 1 in which the optical axis of the source is perpendicular to the image plane.

8. The method of claim 1 wherein the first registration marker and the second registration marker are the same marker.

9. The method of claim 1 wherein the calibration post is substantially transparent to said ray of energy.

10. In a digitized tomosynthesis method for obtaining 3D volumetric imaging of an object in which x-ray radiation from a source travels through the object to impinge on an image plate having a determined pixel size defining an image plane and in which the object is rotated about an axis that intersects the image plate whereby an image is acquired by the image plate at successive rotational positions of the object, the improvement according to which a coordinate of the source position with respect to the image plate is determined, comprising the steps of:

placing a first registration marker that is substantially opaque to the x-ray radiation on a first location proximate the image plate and along the object's axis of rotation;

obtaining a first shadow image corresponding to the first registration marker by exposing the first registration marker to the x-ray radiation;

placing a second registration marker that is substantially opaque to the x-ray radiation on a calibration post that is substantially transparent to said x-ray radiation, to dispose the second registration marker at a location distal from the image plate at a predetermined distance from said first location along the object's axis of rotation;

obtaining a second shadow image of the calibration post corresponding to the second registration marker by exposing the second registration marker to the x-ray radiation;

determining the distance from the source to the image plate at the intersection of the axis with the x-ray radiation;

determining the height of the second marker;

determining central coordinates of the first and second marker shadows;

computing the azimuth from a triangle formed by the marker centers and image axes;

computing the elevation angle by computing an angle A as the arc tangent of (the height of the calibration post divided by the length of the shadow of the calibration post), computing an angle B as the arc sine of (the sine of angle A times the shadow of the calibration post divided by the source distance), computing an angle C as $180°-A-B$, computing a distance c as the square root of $Hp^2$ plus $Ls^2-2.0 \times Hp \times Ls \times cosine (C)$, where Hp is the height of the calibration post and Ls is the length of the shadow of the calibration post, computing the height y of the source above the image plane as $c \times sine (A)$, and computing the elevation angle as arc sine of (y divided by the source distance);

using the elevation angle and azimuth to compute the coordinate of the source position with respect to the image plate.

\* \* \* \* \*